US011969555B2

(12) United States Patent
Hernández

(10) Patent No.: US 11,969,555 B2
(45) Date of Patent: Apr. 30, 2024

(54) METHOD FOR PROVIDING A COMPLEX AUGMENTED REALITY BILATERAL STIMULATION SESSION

(71) Applicant: Rocio Elisa Hernández, San Pablo, CA (US)

(72) Inventor: Rocio Elisa Hernández, San Pablo, CA (US)

(*) Notice: Subject to any disclaimer, the term of this patent is extended or adjusted under 35 U.S.C. 154(b) by 405 days.

(21) Appl. No.: 17/012,408

(22) Filed: Sep. 4, 2020

(65) Prior Publication Data

US 2021/0069459 A1 Mar. 11, 2021

Related U.S. Application Data

(60) Provisional application No. 62/896,907, filed on Sep. 6, 2019.

(51) Int. Cl.
| | | |
|---|---|---|
| *A61M 21/02* | (2006.01) | |
| *A61B 5/00* | (2006.01) | |
| *A61B 5/16* | (2006.01) | |
| *A61M 21/00* | (2006.01) | |
| *G06F 3/0482* | (2013.01) | |
| *G06F 3/0488* | (2022.01) | |
| *G06F 3/16* | (2006.01) | |

(Continued)

(52) U.S. Cl.
CPC ............ *A61M 21/02* (2013.01); *A61B 5/165* (2013.01); *A61B 5/748* (2013.01); *G06F 3/0482* (2013.01);
(Continued)

(58) Field of Classification Search
CPC .......... A61M 21/02; A61M 2021/0027; A61M 2021/005; A61M 2205/3553; A61M 2205/3584; A61M 2210/0612; A61M 2021/0022; A61M 2205/505; A61M 2205/507; A61M 21/00; A61B 5/165; A61B 5/748; A61B 5/4848; G06F 3/0482; G06F 3/0488; G06F 3/165; G06F 3/167; G06Q 50/01; G06T 11/00; G06T 11/60; G06T 2200/24; G09B 5/065; G09B 19/00; G16H 10/20; G16H 15/00; G16H 20/70; G16H 50/70; G16H 30/20; H04N 23/63

(Continued)

(56) References Cited

U.S. PATENT DOCUMENTS

| | | |
|---|---|---|
| 8,261,231 B1 | 9/2012 | Hirsch et al. |
| 10,943,407 B1 | 3/2021 | Morgan et al. |

(Continued)

OTHER PUBLICATIONS

Apple App Store: "EMDR Kit.".

(Continued)

*Primary Examiner* — Sunita Reddy
(74) *Attorney, Agent, or Firm* — Steven R. Vosen

(57) ABSTRACT

A method and apparatus for bilateral stimulation (BLS) is described. An electronic device having at least a display and a camera provides a selection of different BLS sessions for a user. At least one of the sessions uses the camera to provide a real-time scene on the display as the background for the movement of the image of a virtual object. In one configuration, the image moves continuously along pattern on the display. The user either follows the image with their eyes, and/or is required to indicate to the device the position of the image on the display. In another configuration, the image is hidden from view and the user must move the camera within an active area of the display so that the image appears and the user can identify the presence of the image.

5 Claims, 15 Drawing Sheets

(51) Int. Cl.
*G06Q 50/00* (2012.01)
*G06T 11/00* (2006.01)
*G09B 5/06* (2006.01)
*G09B 19/00* (2006.01)
*G16H 10/20* (2018.01)
*G16H 15/00* (2018.01)
*G16H 20/70* (2018.01)
*G16H 50/70* (2018.01)
*H04N 23/63* (2023.01)

(52) U.S. Cl.
CPC ............ *G06F 3/0488* (2013.01); *G06F 3/165* (2013.01); *G06Q 50/01* (2013.01); *G06T 11/00* (2013.01); *G09B 5/065* (2013.01); *G09B 19/00* (2013.01); *G16H 10/20* (2018.01); *G16H 15/00* (2018.01); *G16H 20/70* (2018.01); *G16H 50/70* (2018.01); *H04N 23/63* (2023.01); *A61B 5/4848* (2013.01); *A61M 2021/0027* (2013.01); *A61M 2021/005* (2013.01); *A61M 2205/3553* (2013.01); *A61M 2205/3584* (2013.01); *A61M 2210/0612* (2013.01)

(58) Field of Classification Search
USPC ...................................................... 600/26–28
See application file for complete search history.

(56) References Cited

U.S. PATENT DOCUMENTS

| | | | |
|---|---|---|---|
| 2002/0035995 A1* | 3/2002 | Schmidt | A61M 21/00 128/898 |
| 2004/0161730 A1* | 8/2004 | Urman | G09B 19/00 434/236 |
| 2008/0038706 A1 | 2/2008 | Dameshek | |
| 2010/0323335 A1* | 12/2010 | Lee | A61B 5/16 434/236 |
| 2012/0151319 A1 | 6/2012 | Eastman | |
| 2013/0178257 A1 | 7/2013 | Langseth | |
| 2015/0188958 A1 | 7/2015 | Juristovski et al. | |
| 2016/0220178 A1 | 8/2016 | Rigoard et al. | |
| 2017/0296775 A1* | 10/2017 | Mayo | A61M 21/02 |
| 2018/0318545 A1* | 11/2018 | Jones | A61M 21/02 |
| 2019/0065027 A1* | 2/2019 | Hauenstein | G02B 27/017 |
| 2019/0366031 A1* | 12/2019 | Travers | A61M 21/02 |
| 2020/0086077 A1* | 3/2020 | Gazit | A61H 5/00 |
| 2020/0261688 A1* | 8/2020 | Thoma | A61M 21/02 |
| 2021/0213239 A1* | 7/2021 | Jones | A61M 21/02 |
| 2023/0106753 A1* | 4/2023 | Hanbury | A61M 21/02 600/28 |

OTHER PUBLICATIONS

Apple App Store: "EMDR Therapy.".
Apple App Store: "EMDR for Clinicians.".
Apple App Store: "EMDR 101.".
Website: "Easy EMDR," https://Easy-emdr.com.
Borroteck, "Phobos AR, la app para iOS que combate tus fobiasto," https://www.youtube.com/watch?v=TRWG7Hir0vs, Jun. 2018.
Apple App Store: "Phobos AR," https://apps.apple.com/us/app/phobos-ar/id1281732065, Feb. 27, 2019.
International Search Report and Written Opinion of the International Searching Authority for PCT /US20/49357, dated Feb. 11, 2021.
Co-pending and co-owned U.S. Appl. No. 17/012,407, filed Sep. 4, 2020.

* cited by examiner

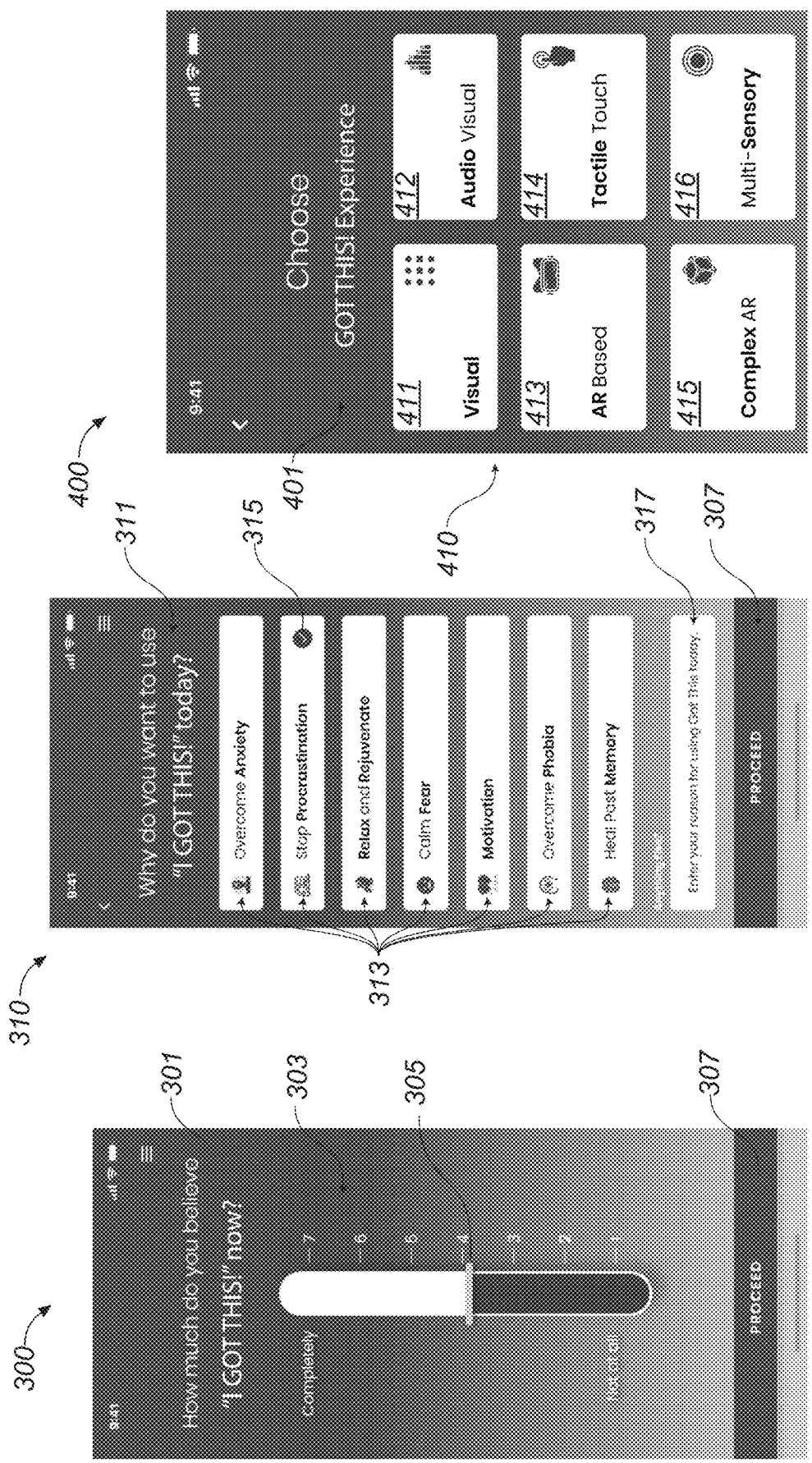

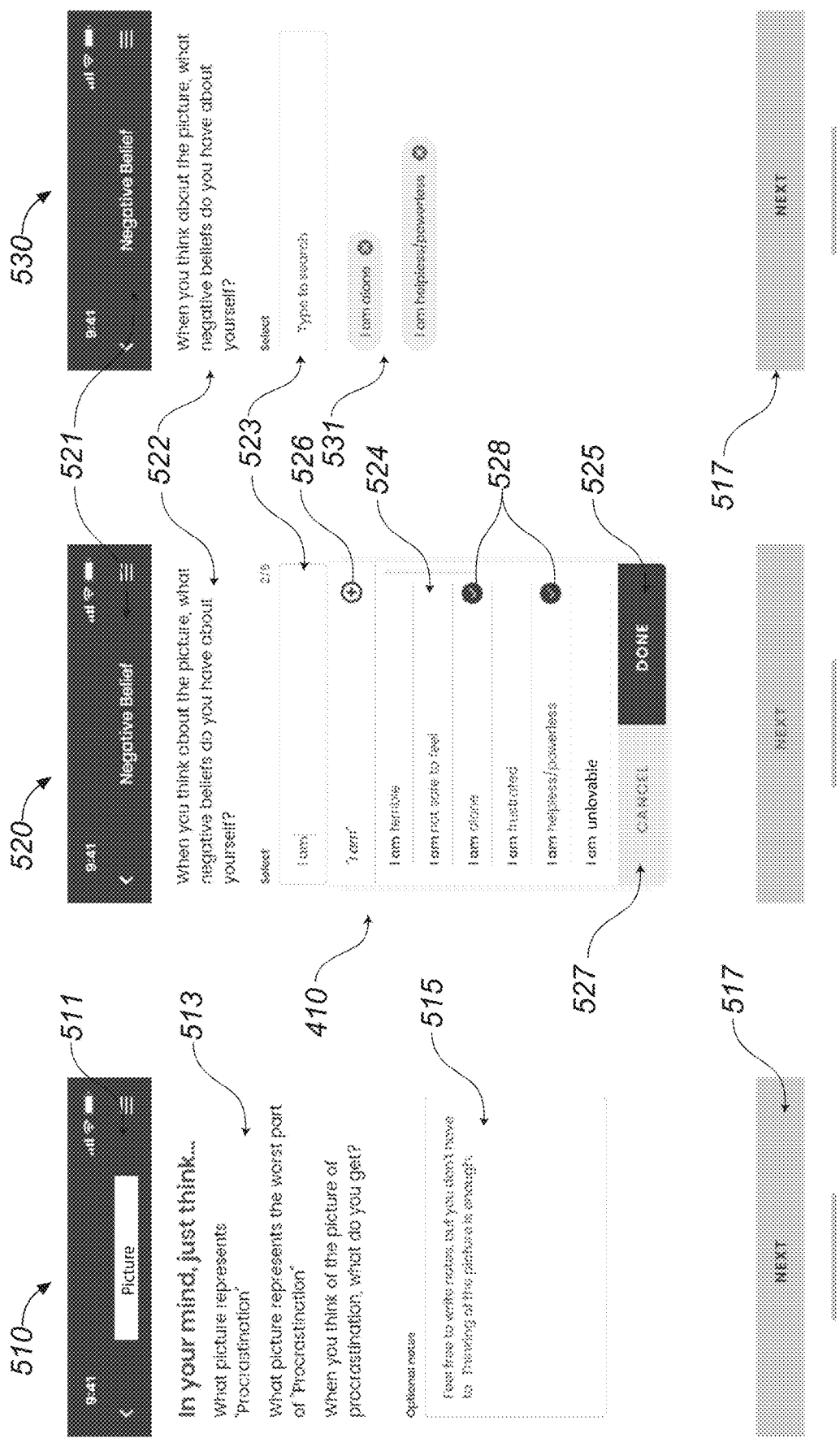

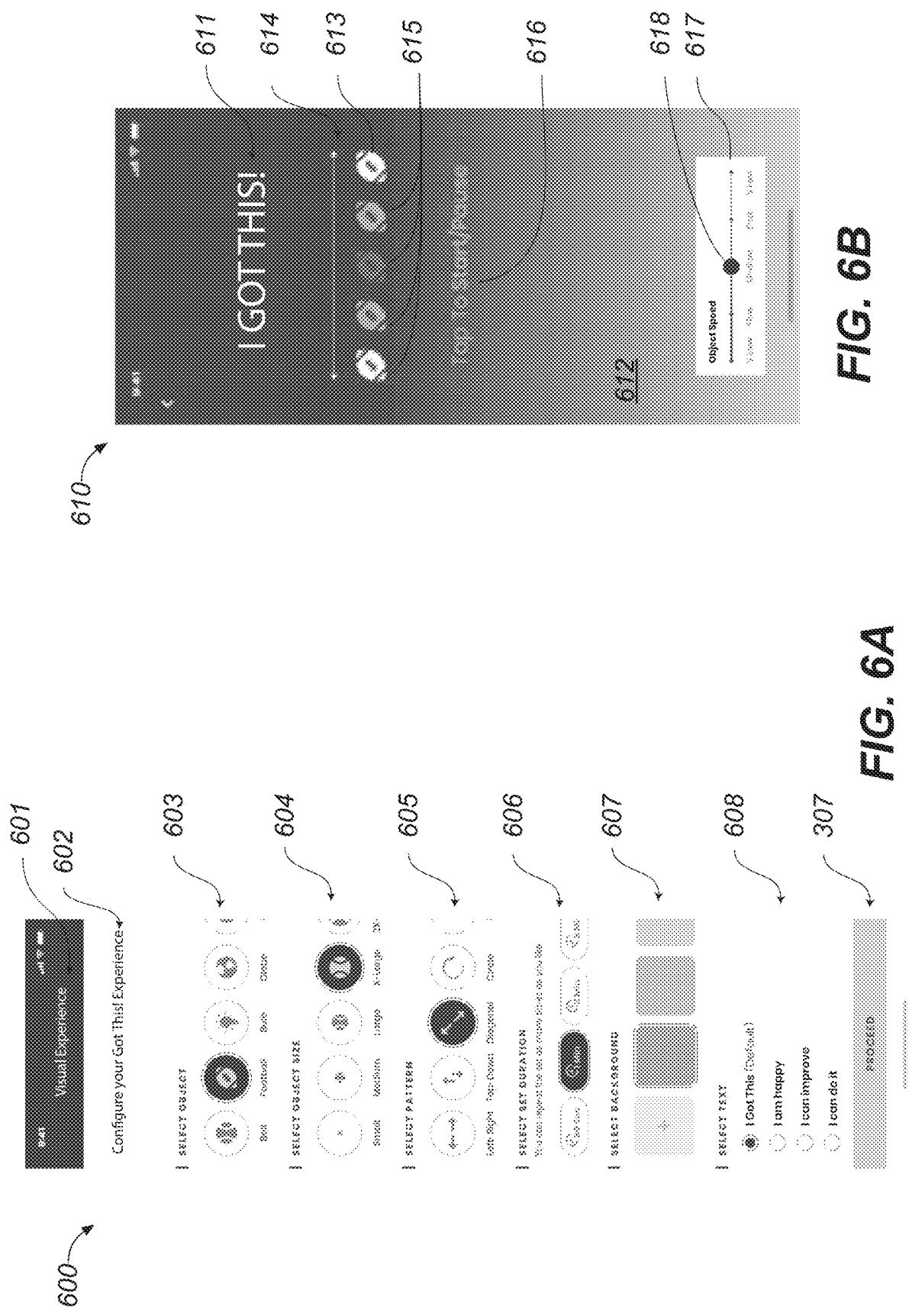

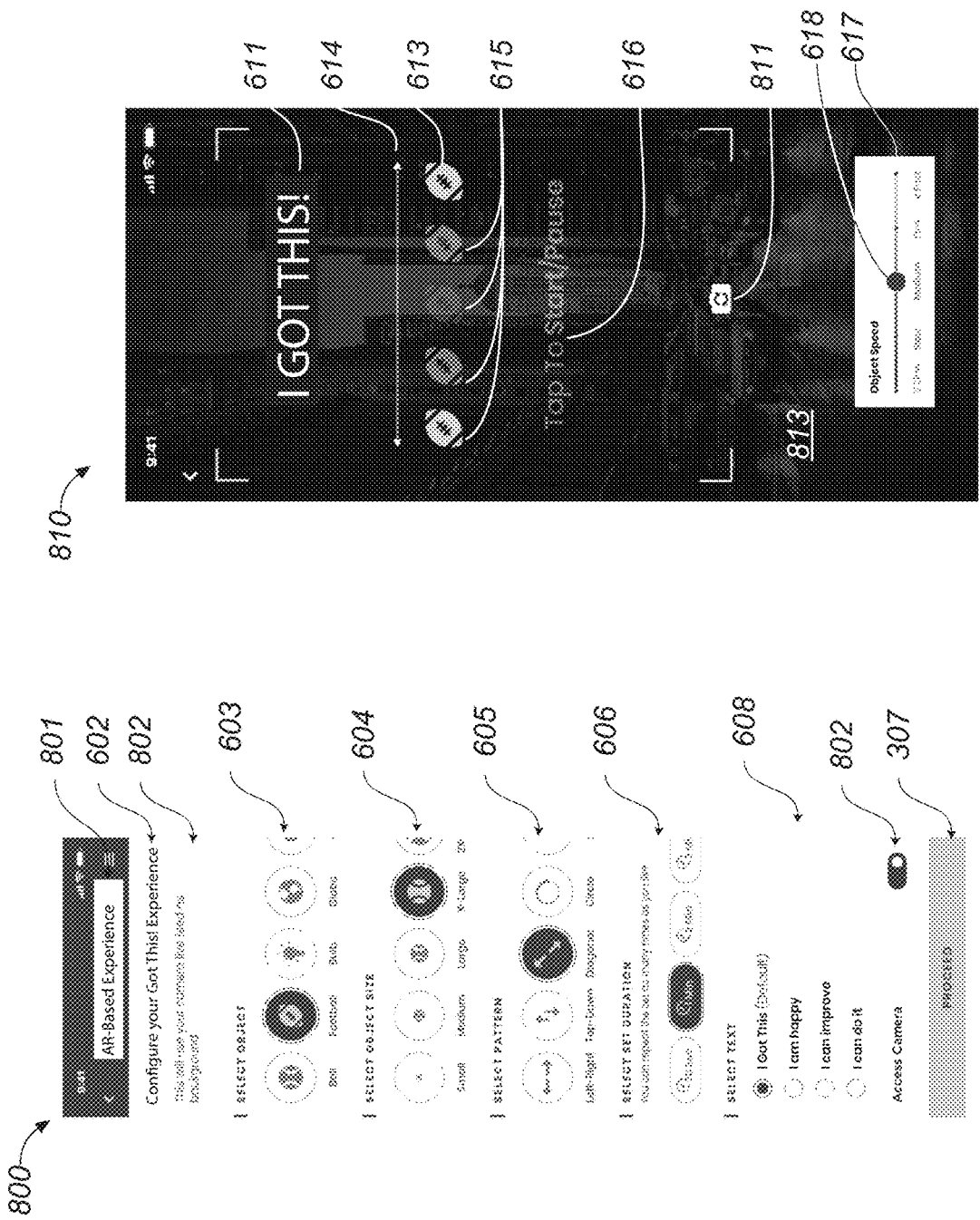

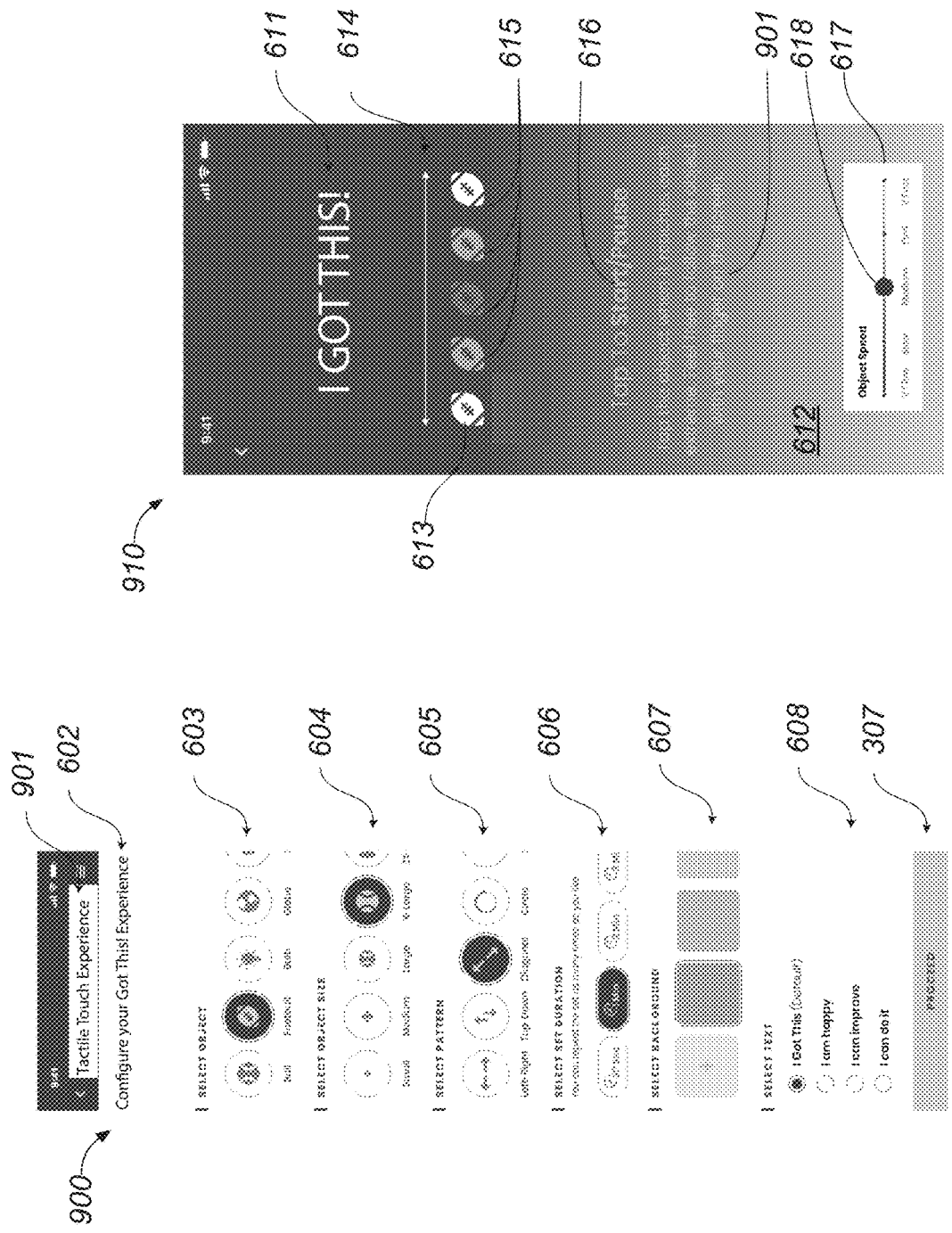

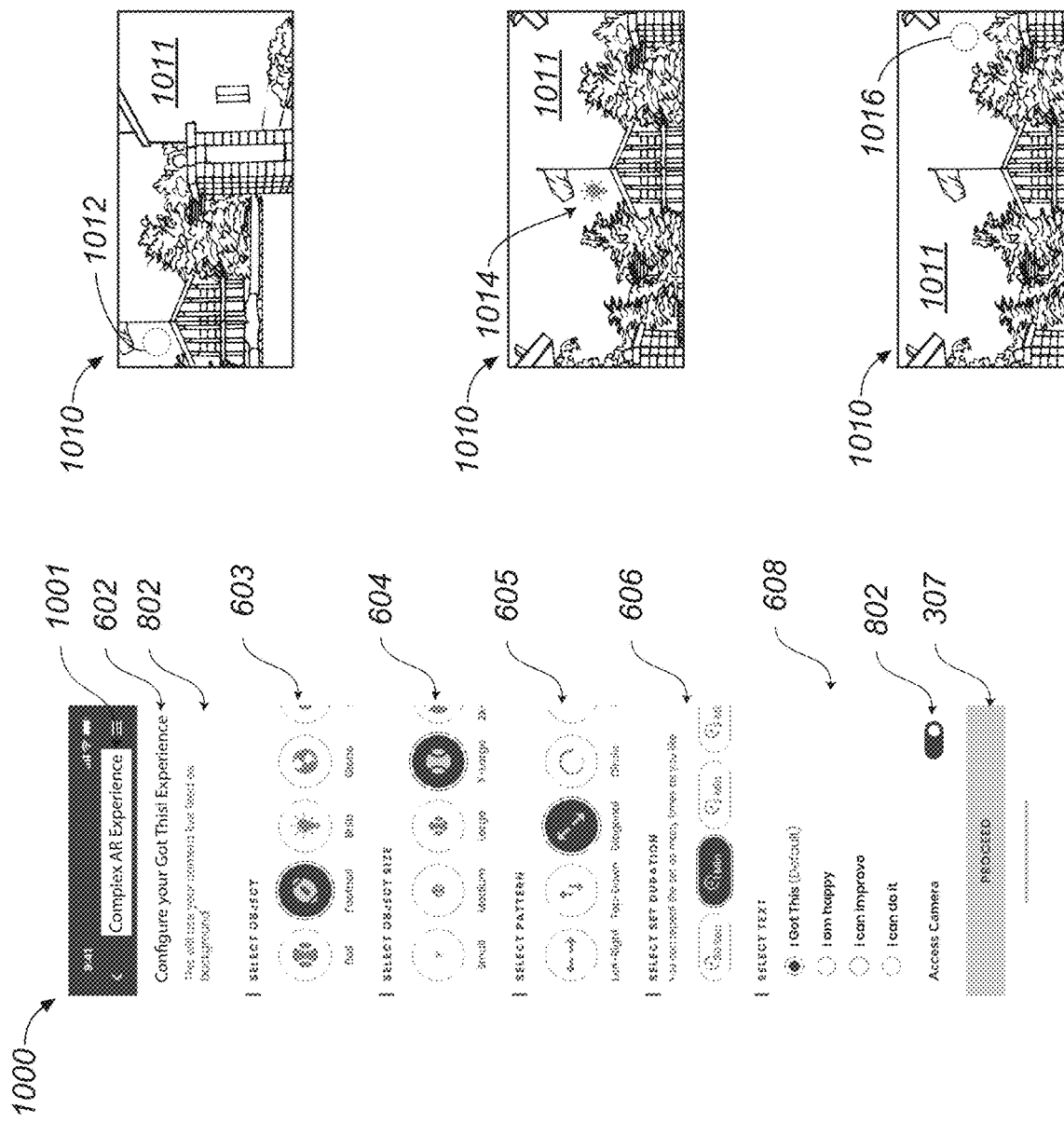

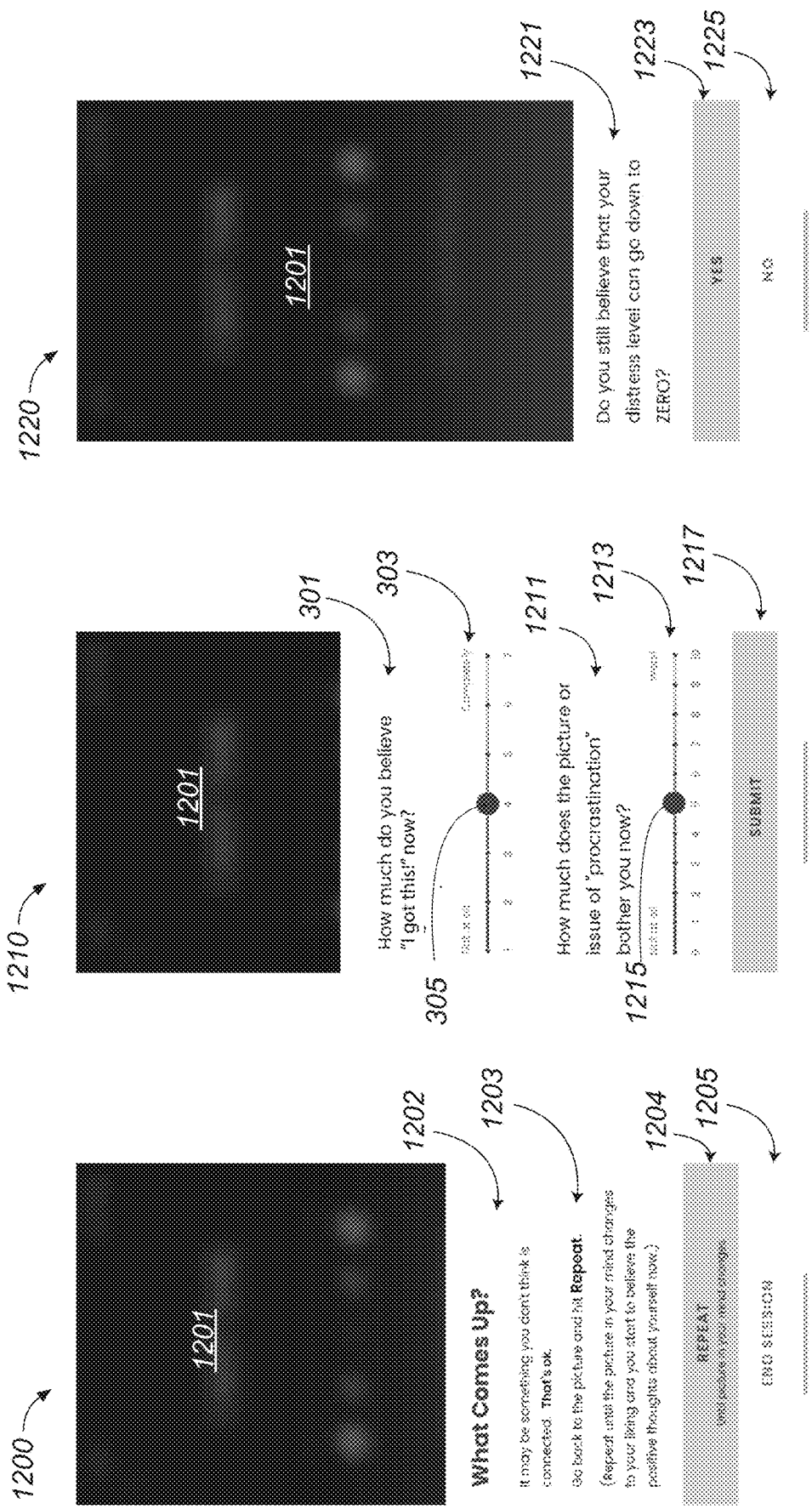

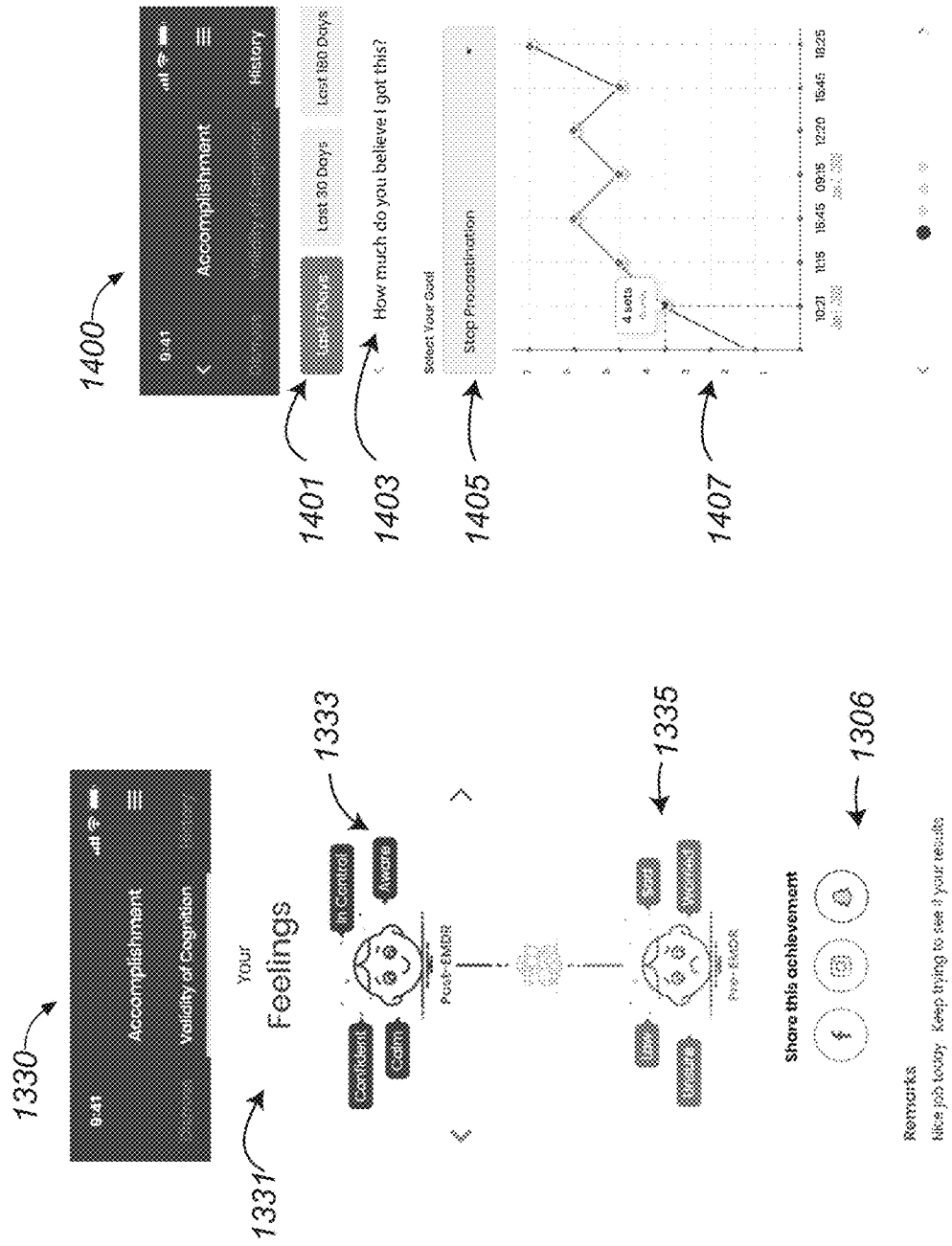

METHOD FOR PROVIDING A COMPLEX AUGMENTED REALITY BILATERAL STIMULATION SESSION

CROSS-REFERENCE TO RELATED APPLICATIONS

This application claims the benefit of U.S. Provisional Application No. 62/896,907 filed Sep. 6, 2019, the contents of which is hereby incorporated by reference in its entirety.

BACKGROUND OF THE INVENTION

Field of the Invention

The present invention generally relates to mental health, and more particularly to a method and system for improving mental health.

Discussion of the Background

Bilateral stimulation ("BLS") is a generalization of a technique for treating people that is a part of the well-known technique of eye movement desensitization and reprocessing ("EMDR") therapy. BLS may be used, for example and without limitation, to achieve certain goals, such as overcome negative beliefs about oneself, overcome fears or reduce the impact of painful memories, such as with post-traumatic stress disorder (PTSD), or reinforcing positive beliefs about oneself.

In a BLS Session the person is instructed to move their eyes in a particular way while, for example, mentally focusing on an image associated with a traumatic experience. It is believed that BLS Sessions in combination with the cognitive identification of feelings and negative beliefs related to the memory or stressful material, and body awareness help to mentally process the memory of the traumatic experience, desensitizing the person to the memory and thus preventing or reducing any associated symptoms.

Several prior art electronic BLS electronic platforms have been developed. While these platforms may be effective, they have several problems. First, prior art platforms provide a limited number of types of stimulation. It is known that people respond differently to different types of stimulation. Providing a limited number of types of stimulation thus limits the effectiveness of the platform for many people. Prior art platforms also provide limited number of objects and backgrounds, and are thus not very compelling to use.

Second, prior art BLS platforms do not have the ability to track the effectiveness of BLS when a person is using the platform to achieve more than one goal. Thus, while some prior art platforms prompt the user for information used to determine the effectiveness of the platform over time, this is not a meaningful metric when a person is using BLS to work on more than one goal.

Thus, there is a need in the art for a method and apparatus that permits for a greater number of choices for providing BLS. There is also a need in the art for a method and apparatus that provides a more engaging environment. Further, there is a need in the art for a method and apparatus that permits users to track the progress when using the platform to address more than one problem or issue. The BLS method and apparatus should be easy to use on a variety of devices.

BRIEF SUMMARY OF THE INVENTION

The present invention overcomes disadvantages of the prior art by providing a method and an apparatus that can be configured by the user to provide a large number of different types of BLS sessions. In certain embodiments, a user may select from a number of backgrounds, objects, and sounds. In certain other embodiments, a user may provide their own background by uploading images or providing access to a device's camera. In certain embodiments, a user may provide their own sound file to provide bilateral audio stimulation.

One embodiment provides method of using an electronic device having a display screen, an input device, and a camera for a BLS session for a user. The method includes: providing the display screen with a prompt to the user to select a BLS session from two or more BLS sessions providing different visual and/or audio stimuli, where each BLS session of the two or more BLS sessions includes moving a position of an image of an object in a pattern on the display screen, and where one of the BLS sessions includes providing a background on the display screen for the image, where the background is a real-time view of the scene obtained from the camera; accepting a user-selected BLS session of the two or more BLS sessions; and providing the user-selected BLS session on the electronic device.

Another embodiment provides an apparatus for providing a BLS session for a user. The apparatus includes: an electronic device including a processor, a display screen, a camera, and an input device, where the processor is programmed to provide the display screen with a prompt to the user to select a BLS session from two or more BLS sessions providing different visual and/or audio stimuli, where for each BLS session of the two or more BLS sessions the processor is programmed to move a position of an image of an object in a pattern on the display screen, and where for one of the BLS sessions the processor is programmed to provide a background on the display screen for the image, where the background is a real-time view of the scene obtained from the camera, accept a user-selected BLS session of the two or more BLS sessions, and provide the user-selected BLS session on the electronic device.

These features together with the various ancillary provisions and features which will become apparent to those skilled in the art from the following detailed description, are attained by the apparatus and method of the present invention, preferred embodiments thereof being shown with reference to the accompanying drawings, by way of example only, wherein:

BRIEF DESCRIPTION OF THE SEVERAL VIEWS OF THE DRAWING

FIGS. 3A and 3B are screenshots to prompt the user for input that are presented to the user after logging in to the system for delivering BLS, where FIG. 3A prompts the user to rate their belief that the system will help them and that they have mastery and control, and FIG. 3B prompts the user for their reasons for using the system;

FIG. 4 is a screenshot prompting the user to select a specific BLS Session;

FIGS. 5A, 5B, 5C, 5D, 5E, 5F, 5G, 5H, and 5I are screenshots prompting the user to answer survey questions before being presented with BLS Session options;

FIGS. 6A and 6B are screenshots prompting a user for input to configure a Visual BLS Session and for providing the user with the configured session, respectively;

FIGS. 8A and 8B are screenshots prompting a user for input to configure an Augmented Reality (AR) BLS Session and for providing the user with the configured session;

FIGS. 9A and 9B are screenshots prompting a user for input to configure a Tactile Touch BLS Session and for providing the user with the configured session;

FIGS. 10A, 10B, 10C, and 10D are screenshots prompting a user for input to configure a Complex AR BLS Session and for providing the user with the configured session;

FIGS. 12A, 12B, and 12C are screenshots prompting a user for feedback related to a completed set;

FIGS. 13A, 13B, 13C, and 13D are screenshots presenting the user with indicators of progress using the inventive system from the most recent user session; and FIGS. 14A, 14B, 14C, and 14D are screenshots presenting the user with historical indicators of progress using the inventive system over some period of time.

Reference symbols are used in the Figures to indicate certain components, aspects or features shown therein, with reference symbols common to more than one Figure indicating like components, aspects or features shown therein.

DETAILED DESCRIPTION OF THE INVENTION

In general, the present invention is a computer-based system for providing a user with BLS. Embodiments are presented herein where a user is provided with BLS on an electronic device, such as a smartphone, tablet, or computer. Additionally, the electronic device may also present a message to the user that is intended to result in a positive belief in themselves (a "positive cognition") which will maximize positive thinking.

Various embodiments provide: the option of selecting and/or configuring a BLS Session; identifying an area that they feel needs improvement, such as overcoming a fear or providing confidence in achieving a goal; optional pre-session and optional post-session surveying to determine the effect of the session on the user; and receiving reports of current or historical measures of the effectiveness of the session.

One embodiment of each of the methods described herein is in the form of a computer program that is stored in computer memory, and which executes on a processing system, e.g., on one or more processors that are part of a networked system.

Figure 2:
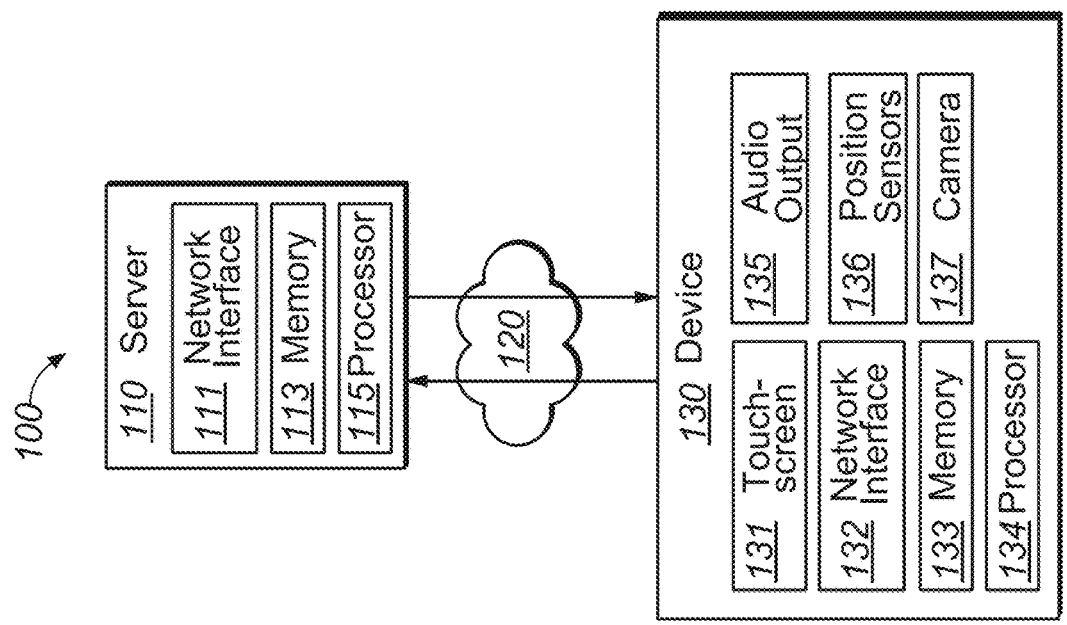
FIGS. 1 and 2 are schematic diagrams illustrative of one embodiment of a system for delivering BLS.
Figure 1:
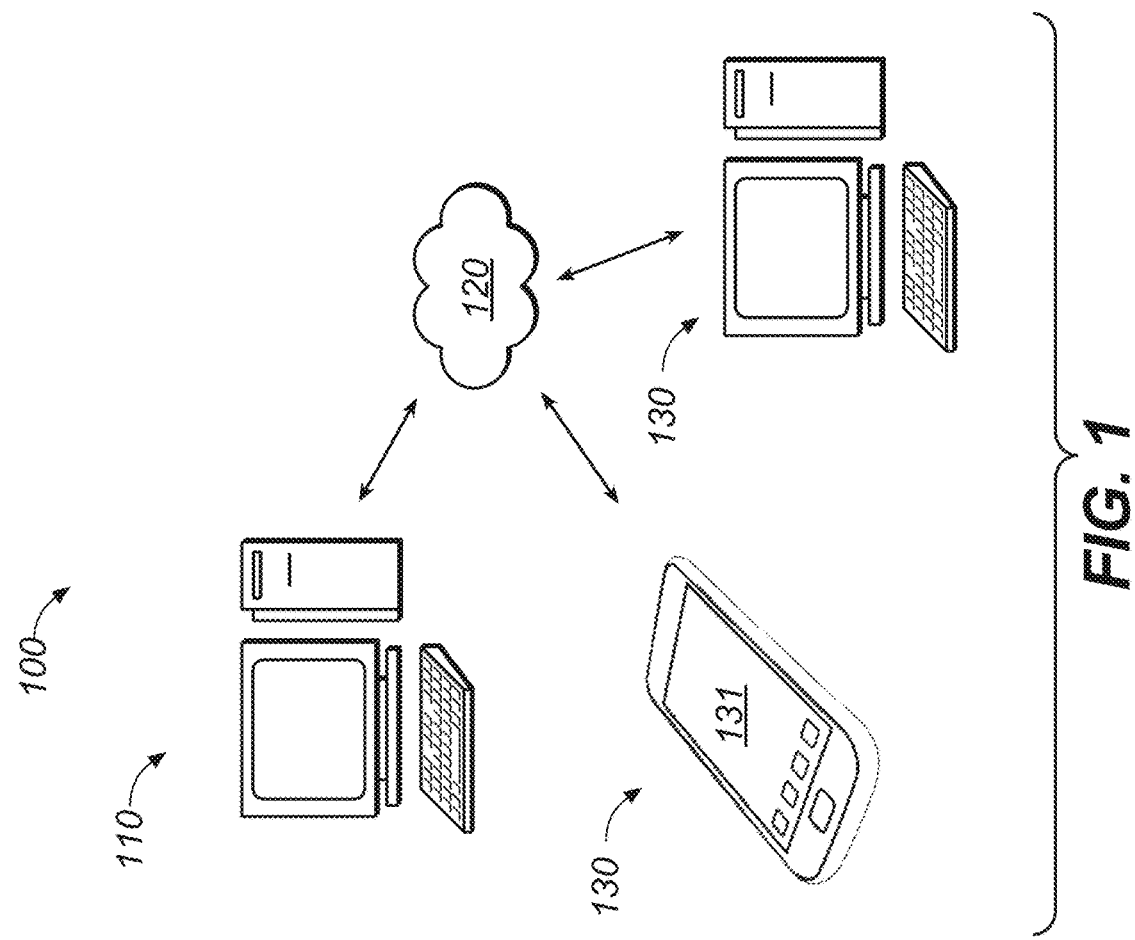

FIGS. 1 and 2 are schematic diagrams which illustrate one embodiment of a system 100 for providing BLS to a user on a device 130, which may be, for example and without limitation, a smartphone, a computer, or on a tablet or some other electronic device. In the following discussion, device 130 will be described, without limitation, as being a smartphone having certain capabilities for providing BLS to a user. It will be understood by those skilled in the art that the features and programming described herein may be modified or eliminated depending on the specific device, and that the discussion here is not meant to limit the scope of the present invention. Thus, for example, some features requiring input from a touchscreen, a gyroscope, or a camera may not be operable on all devices, or may require or use other input devices.

FIG. 2 shows details of system 100, including device 130, which includes a touchscreen 131, a network interface 132, a memory 133, a processor 134, an audio output 135, position sensors 136, which may include a gyroscope, and a camera 137. Memory 133 contains operating instructions of system 100, which processor 134 interprets to operate touchscreen 131 as an input and output device (referred to as a screen or display screen), provide audio to speakers, headphones, or earbuds using audio output 135, to retrieve information from position sensors 136 to determine the orientation of the device in space, and operate camera 137. While the operation of system 100 is described herein with reference to device 130, the system is not limited to the use of devices having the features of device 130. Thus, it will be understood by those in the field that some of the feature of device 130 may be available on all user devices, such as a camera or position sensors, and that some user devices may have other features, such as other input devices.

In certain embodiments, system 100 includes a server 110, or network of servers, and a network 130 that permits device 130 to communicate over network 120 to server 110. Server 110 includes a network interface 111, a memory 113, and a processor 115. In certain embodiments, network interface 132 is used by device 130 to communicate over a wired network or over a wireless network, such as a cellular telephone or Wi-Fi network, and then to other telephones through a public switched telephone network or to a satellite, or over the Internet. Memory 133 includes programming required to operate device 130 (such as an operating system or virtual machine instructions) and may include portions that store information or programming instructions obtained over network interface 132, or that are input by the user (such as telephone numbers or images from a device camera (not shown)). Network interface 111 permits device 130 to receive and transmit information from server 110 for purposes including but is not limited to, downloading apps, web pages, or updates to the user devices, managing access to the system by requiring users to log in or pay a subscription fee for certain features, and maintaining a database of each user's use of system 100.

In certain embodiments, server 110 maintains, in memory 113, a database storing information for each user which may include, for each BLS Session, the session type, configuration and duration, and any information provided to device 130, such as any numeral or text answers to any of the survey or other questions discussed herein. Thus, it will be understood that the input by the user discussed herein is stored in a database that permits analysis and presentation of user input.

The following discussion presents embodiments of system 100 as operating on device 130. Specifically, memory 113 includes stored programming instructions that processor 134 interprets to provide screens and accept input using touchscreen 131, to provide audio using audio output 135, to retrieve images from camera 137 and display the image on the touchscreen, and, over network interface 132 to provide and retrieve information from server 110.

More specifically, programming in memory 133 permits the user to interact with system 100 to perform one or more of the following functions: select a language, which is used by the programming to select the language displayed on touchscreen 131 or provided to audio output 135; to provide warm-ups or tutorials to the touchscreen display or audio output; managing user registration, subscriptions, and login/logout from system 100 by communication with server 110; accepting input from device 130 to select, configure, and operate a BLS Session utilizing the touchscreen, audio output, and/or camera 137; providing optional pre-BLS Session or post-BLS Session surveys on the device, and an optional communication with the server; and reviewing recent and/or historical survey results on the device, either on the device or by communication with the server.

The functioning of system 100 is described herein with reference to figures showing screenshots of the display of touchscreen 131. which are generated by the output generated for display on the touchscreen by programming stored in memory 133. In various embodiments, one or more of the input provided on device 130 is stored in memory 113 or 133 and may be associated with the user. The input so stored may then be used to report on a specific user's progress and/or may be supplied, in some form, subsequently to device 130 to indicate previous choice or provide default settings.

Initial Information Gathering

Prior to providing a BLS Session, system 100 provides the display of touchscreen 131 with several screens to obtain information from the user regarding the session. The results of the initial information gathering, along with the identity of the user, are stored in the memory of system 100.

Thus, for example and without limitation, FIGS. 3A and 3B are screenshots of the display of touchscreen 131 which prompt the user for input regarding the use of system 100.

A first screenshot 300 is shown in FIG. 3A as prompting for an answer to a first initial question and includes a prompt 301, response indicia 303, a user adjustable slider 305, and a "Proceed" prompt 307. Prompt 301 encourages the user to answer the first initial question by indicating their belief that the use of system 100 will help them in solving a particular problem or reaching a particular goal and that they believe in themselves to achieve their goal. In one embodiment, system 100 is branded as an app named GOT THIS!™, and the prompt 301 is "How much do you believe "I GOT THIS" now?" Prompt 301 is intended to rate the user's belief that the system helps the user and they have mastery and control of their situation. Response indicia 303 ranges from "not at all," with a numerical value of 1, to "completely" with a numerical value of 7. The user operates slider 305 to indicate their response and then touches the "Proceed" prompt 307, which after which system 100 will provide a new display on touchscreen 131.

A second screenshot 310 is shown in FIG. 3B as including a message 311, predetermined factors 313, check marks 315, a text input region 317, and "Proceed" prompt 307. Message 311 prompts the user to provide an answer to a second initial question and provide one or more problems or goals that constitute the reason that they are using system 100. The term "factor" as used herein refers, without limitation, to a problem or goal that the user is using system 100 to address. The user may use system 100 in different sessions to address one factor, or the user may address different factors in different sessions.

In one embodiment, message 311 posts the question "Why you want to use Got This! today?" To answer this question, the user may select an answer which, by way of example, and without limitation, is a number of predetermined factors 313 such as "Overcome Anxiety," "Stop Procrastination," "Relax and Rejuvenate," "Calm Fear," "Motivation," "Overcome Phobia," and "Heal Past Memory." In various embodiments, predetermined factors 313 are provided by device 130 or server 110. The user selects one of these factors and a check mark 315 appears on the display screen next to the user-selected factor.

In another embodiment, system 100 responds to the selection of certain factors with a pop-up window or screen to obtain more detailed information about the selected factor. Thus, for example, if the factor "Overcome Phobia" is selected, then a pop-up window may appear with a list of common phobias. This information may be used to provide the user with the selection of objects evocative of the selected phobia.

As described subsequently, the configuration of a BLS session may be modified by the user or system 100 based on the selected factor to improve the effectiveness of the BLS session.

In addition, or alternatively, the user may type a user-supplied factor into text input region 317. Thus, when the user selects region 317, a keyboard (not shown) appears on the display screen and the user may type in a factor, which may be stored in memory 113 or 133 so that the next time that the user uses system 100, the user-supplied factor will appear on the list of predetermined factors 313.

FIG. 4 is a screenshot 400 of the display of touchscreen 131 which prompts the user to select a specific type of BLS Session, and which includes a message 401 and a number of session types 410 in touchscreen regions 411-416. Message 401 prompts the user to choose the type of session. For a Visual BLS Session, the user selects region 411; for an AV BLS Session, the user selects region 412; for an AR Session the user selects region 413; for a Tactile Touch Session the user selects region 414; for a Complex AR Session the user selects region 415, and for a Multi-Sensory Session the user selects region 416.

After selecting one of regions 411-416, system 100 first provides the user with an optional pre-selection survey, as described is the section "PRE-SESSION SURVEY," and then proceeds to provide the selected type of BLS Session.

Pre-Session Survey

Prior to the BLS Session, and regardless of which type of BLS Session was selected from screenshot 400, system 100 first provides the user with an optional pre-session survey. Thus, for example and without limitation, FIGS. 5A-5I are screenshots of the display of touchscreen 131 which system 100 uses to sequentially prompt the user to answer several survey questions related to the user-selected factor as provided to the answer of the second initial question. The results of the pre-session survey, along with the identity of the user, and the configuration of the session are stored in the memory of system 100.

First Pre-Survey Question

FIG. 5A is a screenshot 510 prompting for an answer to a first pre-session survey question to more fully explore the user-selected factor and includes a title 511, a message 513, a notes input region 515, and a "Next" button 517.

Title 511 reads: "Picture," and message 513 is a prompt of the form: "What picture represents "X?" What picture represents the worst part of "X?" When you think of the picture of X, what do you get?" The text inserted in place of X in message 513 corresponds to the underlined words in the user-selected factors provided in response to the second initial question, as discussed with reference to FIG. 3B. The user may enter an optional note in input region 515, and the "Next" press button 517, and system 100 proceeds to a second pre-survey question as described in the section "SECOND PRE-SURVEY QUESTION."

Second Pre-Survey Question

FIGS. 5B and 5C are screenshots 520 and 530, respectively, that prompt the user for answers to a second pre-session survey with questions related to negative beliefs that the user has about themselves, which are also called "negative cognitions," and includes a title 521, a message 522, an input region 523, input suggestions 524, selection check marks 528, a selection, "+" button 526, a "Cancel" button 527, and a "Done" button 525.

Initially the user is presented with screenshot 520, in which title 521 is: "Negative Belief," and message 522 is the prompt: "When you think about the picture, what negative beliefs do you have about yourself?" The user is thus prompted into providing their negative beliefs of themselves when thinking about a picture related to a user-selected factor. The user types their negative belief into input region 523 and presses "+" button 526 to select the input. In certain embodiments, device 130 communicates with server 110 to provide a list of negative cognitions stored in memory 113 that may predict what the user is typing, and which populates input suggestion 524.

The user may tap on one or more of the negative cognitions in region 524, and check marks 528 indicate that these have been selected. The selected cognitions are stored when the user selects a "Done" button 525, or removed by selecting the "Cancel" button 527.

Once "Done" button 525 is selected, screenshot 520 is replaced with screenshot 530 listing selected negative beliefs 531. Individual selected beliefs may be removed by pressing the "x" next to the negative belief and new negative beliefs may be entered into negative beliefs input region 523. The user may press "Next" button 517 and system 100 proceeds to a third pre-survey question as described in the section "3. THIRD PRE-SURVEY QUESTION." to proceed to the next screen.

Alternatively, if a user does not wish to provide any negative beliefs, they may select the "Cancel" button 527 from screenshot 520, and system 100 proceeds to a third pre-survey question as described in the section "THIRD PRE-SURVEY QUESTION."

Third Pre-Survey Question

Figures 5D, 5E, 5F:
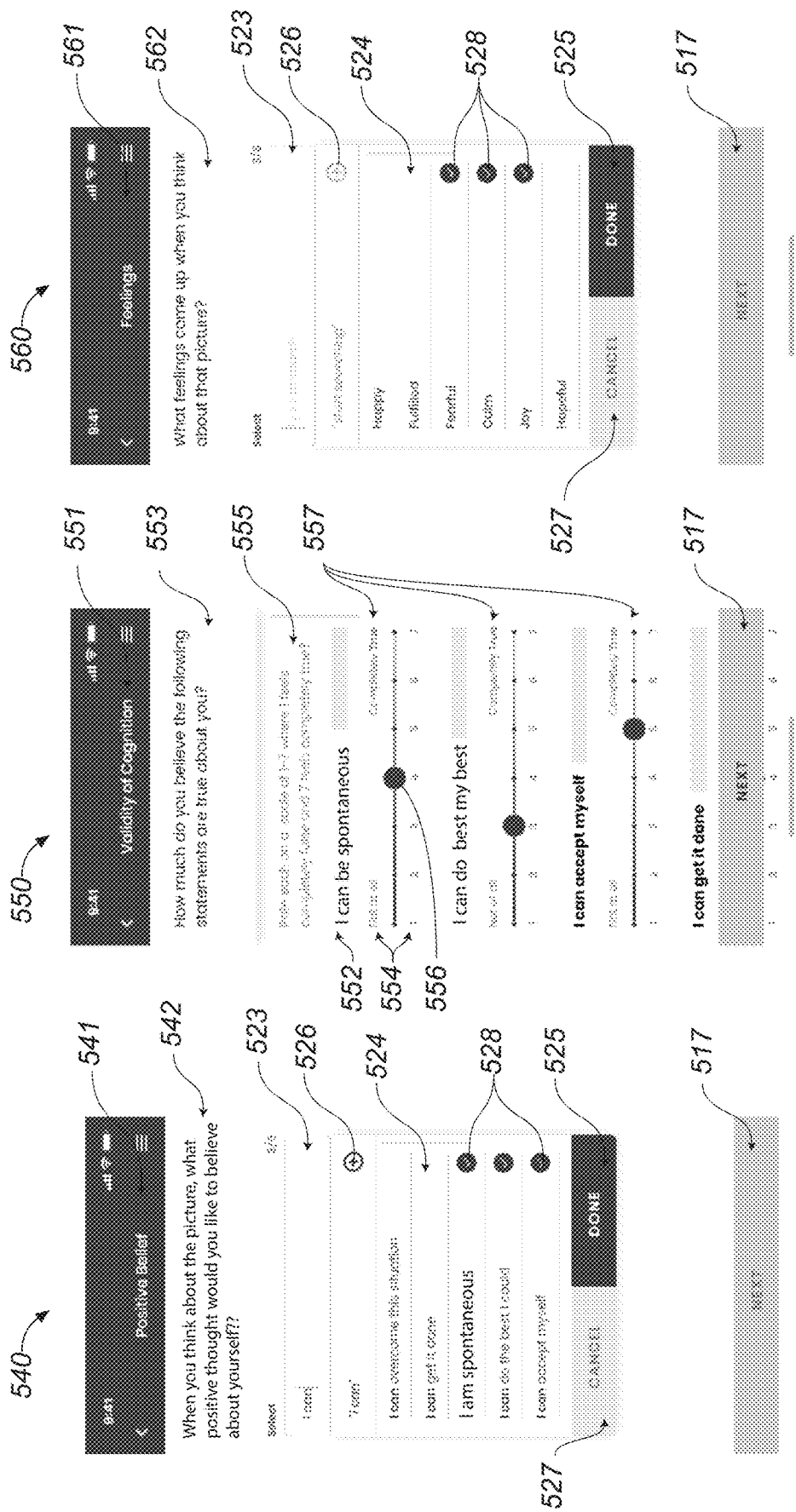

FIG. 5D is a screenshot 540 prompting for an answer to a third pre-session survey question related to positive beliefs. The display screens provided are similar in layout and function to those shown in FIGS. 5B and 5C for negative beliefs, and includes a title 541, a message 542, and includes input region 523, input suggestions 524, selection check marks 528, selection, "+" button 526, "Cancel" button 527, and "Done" button 525, as described above with reference to FIGS. 5B and 5C.

Title 541 is: "Positive Belief," and message 542 is "When you think about the picture, what positive thought would you like to believe about yourself?" The method of completing the third survey question is the same as that discussed above with respect to FIGS. 5B and 5C, but are for positive beliefs. Once the one or more positive beliefs are selected, the user selects "Done" button 525 and then "Next" button 517, and system 100 proceeds to a fourth pre-survey question as described in the section "4. FOURTH PRE-SURVEY QUESTION."

Alternatively, if a user does not wish to provide any positive beliefs, they may select the "Cancel" button 527 from screenshot 540, and system 100 proceeds to a fourth pre-survey question as described in the section "FOURTH PRE-SURVEY QUESTION."

Fourth Pre-Survey Question

FIG. 5E is a screenshot 550 prompting for an answer to fourth pre-session survey questions which relate to the validity of cognition ("VOC") of positive beliefs, obtained from screenshot 540, and includes a title 551, a first message 553, a second message 555, a plurality of statement regions 557 corresponding to each of the selected positive beliefs, and "Next" button 517.

Title 551 is: "Validity of Cognition," first message 553 is the prompt "How much do you believe the following statements are true about you?," and second message 555 are the instructions "Rate each on a scale of 1-7, where 1 feels completely false and 7 feels completely true. Each of the plurality of statement regions includes a label, such as a statement 552, indicia 554 which may include words and numbers, and a slider 556 for responding to the statement.

Examples of the plurality of statement regions 557 are statements 522 including but not limited to: "I can be spontaneous," "I can do my best," "I can accept myself," and "I can get it done." For each statement, the user can adjust the corresponding slider 566 in accordance with the corresponding indicia 554.

Once the user has completed this question, the user selects "Next" button 517, and system 100 proceeds to a fifth pre-survey question as described in the section "FIFTH PRE-SURVEY QUESTION."

Fifth Pre-Survey Question

FIG. 5F is a screenshot 560 prompting for an answer to a fifth pre-session survey question related to the user's feelings. Screenshot 560 is generally similar in layout and function as shown on FIGS. 5B and 5C for negative beliefs, and includes a title 561, a message 562, and includes input region 523, input suggestions 524, selection check marks 528, selection, "+" button 526, "Cancel" button 527, and "Done" button 525, as described above with reference to FIGS. 5B and 5C.

Title 561 is: "Feelings," and message 562 is "What feelings come up when you think about that picture?" The method of completing the third survey question is the same as that discussed above with respect to FIGS. 5B and 5C, but are for feelings. Once the feelings are provided, the user selects "Done" button 525 and then the "Next" button 517 and system 100 proceeds to a sixth pre-survey question as described in the section "6. SIXTH PRE-SURVEY QUESTION."

Alternatively, if a user does not wish to provide any feelings, they may select the "Cancel" button 527 from screenshot 560, and system 100 proceeds a sixth pre-survey question as described in the section "SIXTH PRE-SURVEY QUESTION."

Sixth Pre-Survey Question

Figures 5G, 5H, 5I:
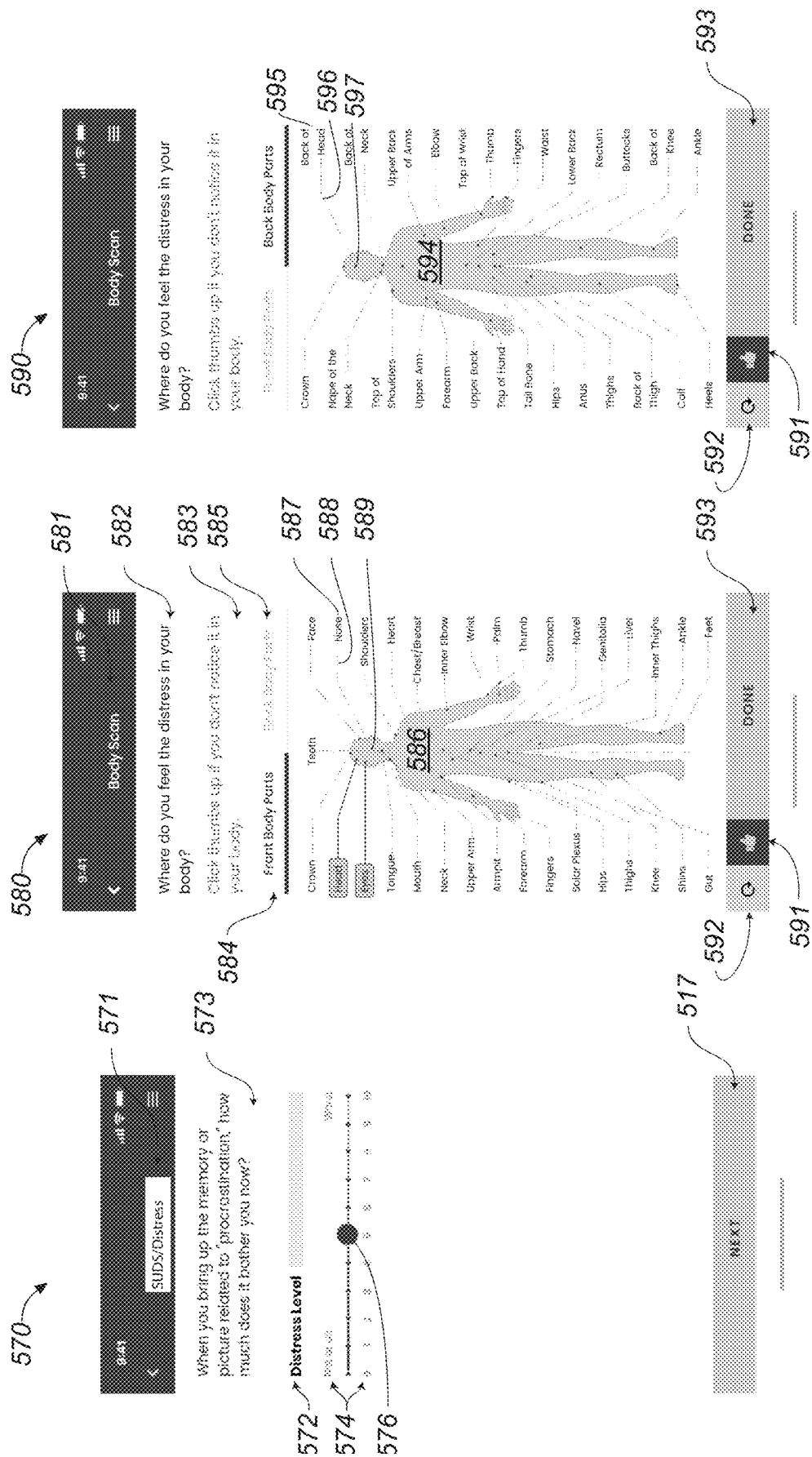

FIG. 5G is a screenshot 570 prompting for an answer to a sixth pre-session survey question to measure a level of distress. The measure may be, for example, a Subjective Units of Distress (SUDS) in which a user assigns a numerical value to their level of distress.

Screenshot 570 includes a title 571, a message 573, a label 572, indicia 574, and a slider 576. Title 571 is: "SUDS Distress," message 573 is the prompt "When you bring up the memory or picture related to "X," how much does it bother you?, where X corresponds to the user-selected, as described above with reference message 513 to FIG. 5A, and where the indicia 574 ranges from "not at all," having a value of "10," to "worst," having a value of "0." The user moves slider 576 to indicate their response and then may press the "Next" button 517, and system 100 proceeds to a seventh pre-survey question as described in the section "SEVENTH PRE-SURVEY QUESTION."

Seventh Pre-Survey Question

FIGS. 5H and 5I are screenshots 580 and 590 prompting answers to a seventh pre-session survey questions related to where the user feels the distress, as provided by the SUDS score, in their body. To aid the user in identifying locations in their body, this survey question includes interactive outlines of the human body.

Screenshots 580 and 590 both have title 581, a first message 582, a second message 583, a first region 584 having an outline of the front of a human body for selecting front body parts, a second region 585 having an outline of the back of the human body for selecting back body parts, a "Thumbs Up" button 591, a refresh button 592, and a "Done" button 593.

Title 581 reads: "Body Scan," first message 582 is a prompt that reads: "Where do you feel the distress in your body?" and second message 583 provides further instructions as "Click thumbs up if you don't notice it in your body." The user switches between screenshots 580 and 590 by selecting regions 584 and 585, respectively. When first region 584 is selected, screenshot 580 provides a front body outline 586, a plurality of front body labels 587, body location indicators 589, and callout lines 588 between each label and indicator. When second region 585 is selected, screenshot 590 provides a back body outline 594, a plurality of back body labels 595, body locations indicators 597, and callout line 596 between each label and indicator.

The user answers the prompt of first message 582 by switching between screenshots 580 and 590 and selecting as many labels 587 and/or 595 necessary to respond to the prompt, or selects "Thumbs Up" button 591 to indicate that no body feeling was present. Selecting the refresh button de-selects all the body parts.

The user may press a "Done" button 593 and system 100 proceeds to provide the type of BLS Session selected from regions 411-416 of screenshot 400. Thus, if the user selected region 411 for a Visual BLS Session, then the system 100 next proceeds as described in the section titled "VISUAL BLS SESSION;" if the user selected region 412 for an AV BLS Session, then the system next proceeds as described in the section titled "AV BLS SESSION;" if the user selected region 413 for an AR BLS Session, then the system next proceeds as described in the section titled "AR BLS SESSION;" if the user selected region 414 for a Tactile Touch BLS Session, then the system next proceeds as described in the section titled "TACTILE TOUCH BLS SESSION;" if the user selected region 415 for a Complex AR BLS Session, then the system next proceeds as described in the section titled "COMPLEX AR BLS SESSION;" and if the user selected region 416 for a Multi-Sensory BLS Session, then the system next proceeds as described in the section titled "MULTI-SENSORY BLS SESSION."

BLS Sessions

Visual BLS Session

A Visual BLS Session is a session in which the user is presented with an object on the display screen that moves on in a repeated pattern on the display screen against a background pattern. The pattern is a motion that moves between one extreme position on the display screen, and may be for example and without limitation, a left-right motion, an up-down motion, or a diagonal motion. Alternatively, the pattern may be an oval or a figure-8 shape. During the Visual BLS Session the user follows the object as it traverses the pattern.

If the user selected region 411 for a Visual session, then system 100 executes the steps required to configure and provide a Visual BLS Session. A Visual BLS Session provides an object that repeatedly traces a pattern on the touchscreen. This section describes how system 100 configures and provides a Visual BLS Session.

First, screenshot 600, as shown in FIG. 6A, is provided on the display of touchscreen 131. Screenshot 600 prompts a user to configure the Visual BLS Session, with a title 601, a message 602, regions 603-608 for configuring the Visual BLS Session, and a "Proceed" button 307. Title 601 is "Visual Experience," and message 602 is the prompt "Configure your Got This! Experience." Each one of regions 603-608 includes a number of items for configuring the session and permits the user to select one item in each of the regions.

Region 603, labeled "Select Object," presents a plurality of objects, one of which may be chosen to be a user-selected object for display on touchscreen 131 during the session. In one embodiment, region 603 presents a number of objects determined by system 100, which include but is not limited to various types of balls, a light bulb, and a globe. In another embodiment, region 603 presents a dialog box that permits the user to upload an image of an object from device 130, server 110, or from the Internet. In yet another embodiment, region 603 presents a dialog box that permits the user to choose an image obtained from camera 137 as the object image.

Region 604, labeled "Select Object Size," presents a plurality of size choices, one of which may be selected for the user-selected object.

Region 605, labeled "Select Pattern," presents a plurality of trajectory patterns for the user-selected object across touchscreen 131, one of which may be selected as the trajectory of the selected object. The user-selected trajectory patterns may include but are not limited to: left-right, top-down, diagonal, circle, oval, and figure-8. The trajectory pattern includes two or more predetermined positions on the display screen, and the trajectory of the user-selected object on touchscreen 131 is provided by the object moving from one of the predetermined positions to the other.

Region 606, labeled "Select Set Duration," presents a plurality of set durations, one of which may be selected as the duration of one set repetition of the experience. Each session includes at least one set which may be repeated at the user's and/or system's discretion, as discussed subsequently. In yet another embodiment, region 606 presents a dialog box that permits the user to enter a set duration of their choosing.

Region 607, labeled "Select Background," presents a plurality of backgrounds, one of which may be chosen as the user-selected background against which the object moves during the session. In one embodiment, region 607 presents several backgrounds determined by system 100. In another embodiment, region 607 presents a dialog box that permits the user to upload an image or video background from device 130, server 110, or from the Internet. In yet another embodiment, region 607 presents a dialog box that permits the user to choose an image or video obtained from camera 137 as the background.

Region 608, labeled "Select Text," presents a plurality of text messages, one of which may be chosen as the user-selected message, and which is displayed during the session. In addition to a default text ("I Got This!"), other selections correspond to the positive beliefs provided during the pre-session survey (see discussion of FIG. 5D). In one embodiment, region 608 presents a number of text selections determined by system 100. In another embodiment, region 607 presents a dialog box that permits the user to enter a text message from device 130.

In certain embodiments, one or more of regions 603-608 are modified by current or previous information provided by the user to system 100. Specifically, BLS outcome is improved if the object is related to the selected factor. Thus, in one embodiment, if the user selects the predetermined factor of "Overcome Phobia," then system 100 provides region 603 with objects that correspond to the phobia, such as an image of a spider, or an airplane.

Once the user has configured the session and "Proceed" button 307 is selected, screenshot 610, as shown in FIG. 6B, is provided on the display of touchscreen 131.

Screenshot 610 is used for the Visual BLS Session, and includes a message 611, which corresponds to the user-selected message from region 608, a background 612 which corresponds to the selection from region 607, and an object 613 which corresponds to the selection from region 603 with size selected in region 604, and an input region 616 labeled "Tap to Start/Pause" Screenshot 610 is schematic, it includes a trajectory pattern 614, which corresponds to the selection from region 605 and objects 615 indicating the trajectory of object 613 which are for reference for this discussion and which are not visible on touchscreen 131 during a session. Screenshot 610 also shows an object speed pop up window 617 having a slider 618.

Once the user selects region 616, selected object 613 having the selected size, appears on touchscreen 131 and moves back and forth, or around, according to the selected trajectory. Specifically, during the Visual BLS Session, object 613 moves according to the selected trajectory 614 against the selected background 612 and with a selected message 611, for the selected duration 606. The speed of object 613 on trajectory 614 is preset.

When a user activates touchscreen 131, pop up window 617 appears and the user may adjust the speed of the object by moving slider 618. If the user selects "Tap to Start/Pause" (region 616) during a session, or if the session has reached the end of the set duration, then system 100 determines the next action, as described below with reference to FIGS. 12A-12C, as discussed subsequently.

AV BLS Session

An AV BLS Session is a session that includes a moving object, as described above with respect to the Visual BLS Session, and also includes an audio track that the user listens to while the object is moving. In certain embodiments, the audio alternates between the left and right ear in time with the motion of the object from one extreme position and the other extreme position.

If the user selected region 412 for an AV session, then system 100 executes the steps required to configure and provide a Visual BLS Session. A Visual BLS Session provides an object that repeatedly traces a pattern on the touchscreen. This section describes how system 100 configures and provides an AV BLS Session.

Figures 7A, 7B:
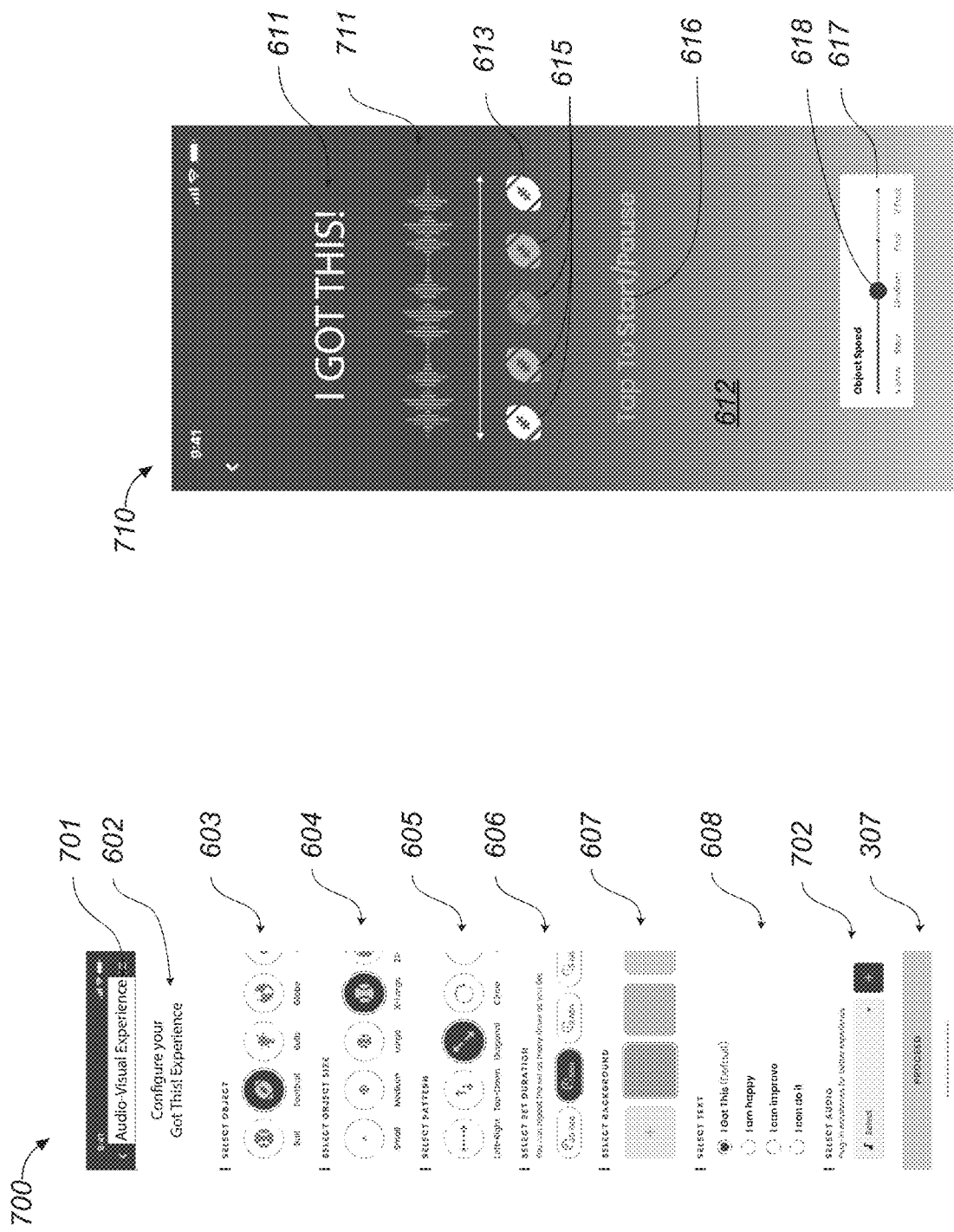
FIGS. 7A and 7B are screenshots prompting a user for input to configure an Audio-Visual ("AV") BLS Session and for providing the user with the configured session.

First, a screenshot 700, as shown in FIG. 7A, is provided on the display of touchscreen 131. Screenshot 700 prompts a user to configure the AV BLS Session, and is generally similar to screenshot 600, except as explicitly stated. Specifically, screenshot 700 include a title 701 ("Audio-Visual Experience"), message 602, regions 603-608, a region 702 for configuring the AV BLS Session, and "Proceed" button 307.

Regions 603-608 as described above, configure the visual component of the AV BLS Session. Region 702 configures the audio component of the AV BLS Session. Specifically, region 702 provides for the user to select one of a variety of audio tracks. In an alternative embodiment, region 702 allows a user to indicate an audio track from one stored on their device or obtained over the Internet.

Once the user has configured the session and "Proceed" button 307 is selected, screenshot 710, as shown in FIG. 7B, is provided on the display of touchscreen 131.

Screenshot 710 is used for the AV BLS Session, and is generally similar to screenshot 610. Screenshot 710 is schematic, in that it includes a trajectory and audio pattern 711, which corresponds to the selection from region 605 and objects 615 indicating the trajectory of object 613 which are for reference for this discussion and which are not visible on touchscreen 131 during a session.

The operation of system 100 in providing an AV BLS Session differs from a Visual BLS Session in that device 130 provides the audio track selected in region 702 to audio output 135, which the user preferentially listens to through headphones or earbuds. Once the user selects region 616, selected object 613 having the selected size, appears on touchscreen 131 and moves back and forth, or around, according to the selected trajectory. In addition, as the object 613 traces trajectory pattern 711 represents the left and right audio channels as they shift back and forth. For left-right object trajectory pattern, the audio tracks the object in the left and right channels. For other object trajectory patterns, the audio is synched to the object in that the audio shifts from left to right and back to left and the object goes from a first position to a second position and back to the first position.

If the user selects "Tap to Start/Pause" (region 616) during a session, or if the session has reached the end of the set duration, then system 100 determines the next action, as described below with reference to FIGS. 12A-12C, as discussed subsequently.

AR BLS Session

An AR BLS Session is a session that includes a moving object, as described above with respect to the Visual BLS Session, and where a real-time view from the camera of the device is provided as a background. By incorporating the view from the camera into the BLS session, users may address a stressor, goal, or memory from their own environment. Thus, for example, if factor is anxiety about being in a certain location, the use of the camera allows a real-time image of that location to be part of the BLS session, and thus assists the user in overcoming anxiety about that location.

If the user selects region 413 for an AR BLS Session, then system 100 executes the steps required to configure and provide an AR BLS Session. An AR BLS Session is generally similar to Visual BLS Session, as described above, with background 612 replaced with an image provided by camera 137. This section describes how system 100 configures and provides an AR BLS Session.

First, a screenshot 800, as shown in FIG. 8A, is provided on the display of touchscreen 131. Screenshot 800 prompts a user to configure the AV BLS Session, and is generally similar to screenshot 600, except as explicitly stated. Specifically, screenshot 800 includes a title 801 ("AR-Based Experience"), message 602, a message 802 ("This will use the camera live feed for the background"), regions 603-606 and 608, a button 802 to grant access to the camera, and "Proceed" button 307.

Regions 603-606 and 608 as described above, configure the visual component of the AV BLS Session. The user is required to provide access to camera 137 by toggling button 802.

Once the user has configured the session and "Proceed" button 307 is selected, screenshot 810, as shown in FIG. 8B, is provided on the display of touchscreen 131.

Screenshot 810 is used for the AR BLS Session, and is generally similar to screenshot 610, and also includes a front/rear button 811 to select a frontward or rearward facing camera, and background 813, which is the view through the camera.

If the user selects "Tap to Start/Pause" (region 616) during a session, or if the session has reached the end of the set duration, then system 100 determines the next action, as described below with reference to FIGS. 12A-12C, as discussed subsequently.

Tactile Touch BLS Session

A Tactile Touch BLS Session is a session that includes a moving object, as described above with respect to the Visual BLS Session and which requires user input during the session. Specifically, when the object reaches an extreme position on the display screen, the motion of the object stops until the user selects the object on the display screen, at which time the object resumes moving towards the next extreme position. They may also follow the object by dragging their finger on the display screen along the trajectory of the object.

If the user selected region 414 for a Tactile Touch BLS Session, then system 100 executes the steps required to configure and provide an Tactile Touch BLS Session. A Tactile Touch bilateral stimulus session is generally similar to Visual BLS Session, as described above, except that it requires user input on touchscreen 131 during a session, as described subsequently. This section describes how system 100 configures and provides a Tactile Touch BLS Session.

First, a screenshot 900, as shown in FIG. 9A, is provided on the display of touchscreen 131. Screenshot 900 prompts a user to configure the Tactile Touch stimulation session, and is generally similar to screenshot 600, except that it includes a title 901 ("Tactile Touch Experience"). The other regions and inputs accepted are the same as for screenshot 600.

Once the user has configured the session and "Proceed" button 307 is selected, screenshot 910, as shown in FIG. 9B, is provided on the display of touchscreen 131.

Screenshot 910 is used for the Tactile Touch BLS Session, and is generally similar to screenshot 610, and also includes a message 910, which is: "Tap the object when it reaches each extreme. Feel free to follow the object with your finger on the display screen."

The operation of system 100 in providing an Tactile Touch BLS Session is different from the Visual BLS Session in that the object motion is discontinuous. Specifically, the object traces the pattern and then stops at certain predetermined locations, which may be 1, 2, 3, or more different locations, and waits for the user to locate the object on the display screen before continuing to move. Thus, for example, the object may move from one extreme location of the pattern to another extreme location and then stop. System 100 then, via touchscreen 131, senses that the user has touched the object, and the motion of the object continues. In other words, system 100 senses if the user has touched the object at a position where motion has halted before continuing with a trajectory along the pattern. In certain embodiments, native AR libraries are used to determine when to accept such input.

If the user selects "Tap to Start/Pause" (region 616) during a session, or if the session has reached the end of the set duration, then system 100 determines the next action, as described below with reference to FIGS. 12A-12C, as discussed subsequently.

Complex AR BLS Session

If the user selected region 415 for a Complex AR BLS Session, then system 100 executes the steps required to configure and provide a Complex AR BLS Session. A Complex AR BLS Session is a session in which the user must find virtual objects in a scene. A Complex AR BLS session may allow the BLS session to overload the working memory while holding the distressing material in the mind by simultaneously displaying a real-time view while requiring the user to find hidden objects.

Complex AR BLS Sessions provide, sequentially, a hidden virtual object which the user must find by pointing camera 137 towards the location of the hidden virtual object, which reveals the virtual object, and then selecting the virtual object from the touchscreen. Thus, for example, system 100 places a hidden virtual object at a computed scene location as viewed by camera 137 and then waits for the user to position device 130 at the scene location, displays the virtual object at the scene location, waits for the user to select the displayed virtual object, and then computes a next location for the hidden virtual object.

In one embodiment, system 100 is programmed to perform the following steps: 1) determine a location of the virtual object, where the location is relative the surrounding scene; 2) determine an active area on the touchscreen corresponding to the virtual object; 3) without presenting the image of the virtual object on touchscreen 131 and as the user moves camera 137, use position sensors 136 to track the location of the virtual object; 4) when the location of the virtual object in the scene is within the active area on the display, present the image of the virtual object on the touchscreen; 5) wait for the user to select or otherwise indicate that the image of the object has been found using the touchscreen as described above regarding the Tactile Touch BLS Session; 6) when the user has selected the image of the virtual object from the touchscreen, as described above for example, regarding the Tactile Touch BLS session, remove the image of the virtual object from the touchscreen. System 100 is then programmed to select the next location for the virtual object and the active display area and repeats the steps outlined above.

In certain embodiments, when the location of the next virtual object is determined, it is within the scene on the display. In certain other embodiments, when the location of the next virtual object is determined, it is not within the scene on the display—that is, it is "off-camera." In certain embodiments, the active area changes with the virtual objects, and may be, for example, at the center of the display or at some other location. In certain other embodiments, the active area is the same for all virtual objects, and may be, for example, at the center of the display or at some other location. In certain embodiments, the user is provided with audio through audio output 135.

By way of example, FIG. 10A is a screenshot prompting a user for input to configure a Complex AR BLS Session. Configuring a Complex AR BLS Session is, in certain circumstances, the same as the configuration of an AR BLS Session. A screenshot 1000, as shown in FIG. 10A, is provided on the display of touchscreen 131. Screenshot 1000 prompts a user to configure the Complex AR BLS Session, includes a title 1001 ("Complex AR Experience"), and also includes messages 602 and 802, regions 603-606 and 608, and buttons 802 and 307, and provides functions similar to the same FIGS. 10B, 10C, and 10D are screenshots 1010 illustrating system 100 providing a Complex AR BLS Session. Screenshot 1010 includes an image 1011 of a scene obtained from camera 137. System 100 first determines a first position of the selected virtual object in the scene of image 1011. The first position may be within the current view of the scene, or may be "off-camera" and not within the current view of the scene. By way of example, which is not meant to be limiting, a dashed circle 1012 in FIGS. 10B-10D show the first position of the virtual object in the scene of image 1011 and an active area 1013. Dashed circle 1012 and active area 1013 are shown for illustrative purposes, and are not visible on touchscreen 131

Next, the user attempts to find the hidden object by moving device 130. As the user moves device 130, system 100 combines the fixed position of the virtual object in the scene and position sensors 136 to determine where circle 1012 appears on touchscreen 131 as device 130 is moved. As illustrated in FIG. 10C, when the user points camera 137 such that circle 1012 aligns with active area 1013, system 100 responds by generating an image of the virtual object 1014 on the touchscreen 131. Thus, it is noted that the circle 1012 and virtual object 1014 are in the same position in the scene shown in image 1011.

System 100 then uses touchscreen 131 as an input device and waits until the user selects the virtual object 1014. In certain embodiments, native AR libraries are used to determine when to accept such input.

Once the virtual object is selected, system 100 determines a next fixed position of the selected virtual object in the scene of image 1011 according to the selected object pattern. FIG. 10D illustrates the position of the next fixed position as dashed circle 1016. As discussed above with regard to FIG. 10B, dashed circle 1012 is shown to indicate a computed location and is not visible on touchscreen 131.

In one embodiment, system 100 determines the sequential locations of the virtual object as being, alternatively, on the left or right side of touchscreen 131. In certain embodiments, the locations are within the visible scene. In certain other embodiments, the virtual object may be placed off-screen and thus out of the view of camera 137. In other embodiments, the sequential locations of the virtual objects follow the shape of the selected object pattern.

If the user selects "Tap to Start/Pause" (region 616) during a session, or if the session has reached the end of the set duration, then system 100 determines the next action, as described below with reference to FIGS. 12A-12C, as discussed subsequently.

Multi-Sensory BLS Session

If the user selected region 416 for a Multi-Sensory BLS Session, then system 100 executes the steps required to configure and provide a Multi-Sensory BLS Session.

Figure 11B:
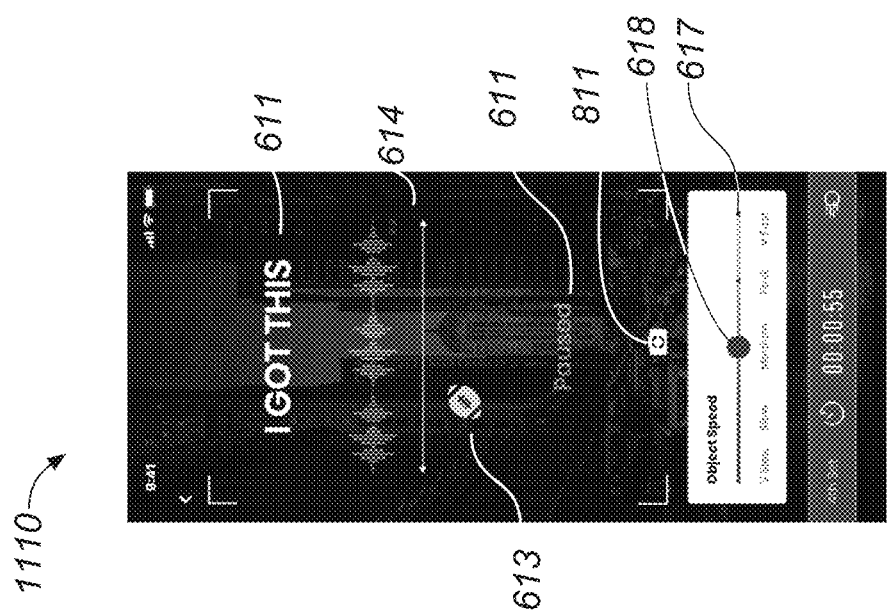
FIGS. 11A and 11B are screenshots prompting a user for input to configure a Multi-Sensory BLS Session and for providing the user with the configured session.
Figure 11A:
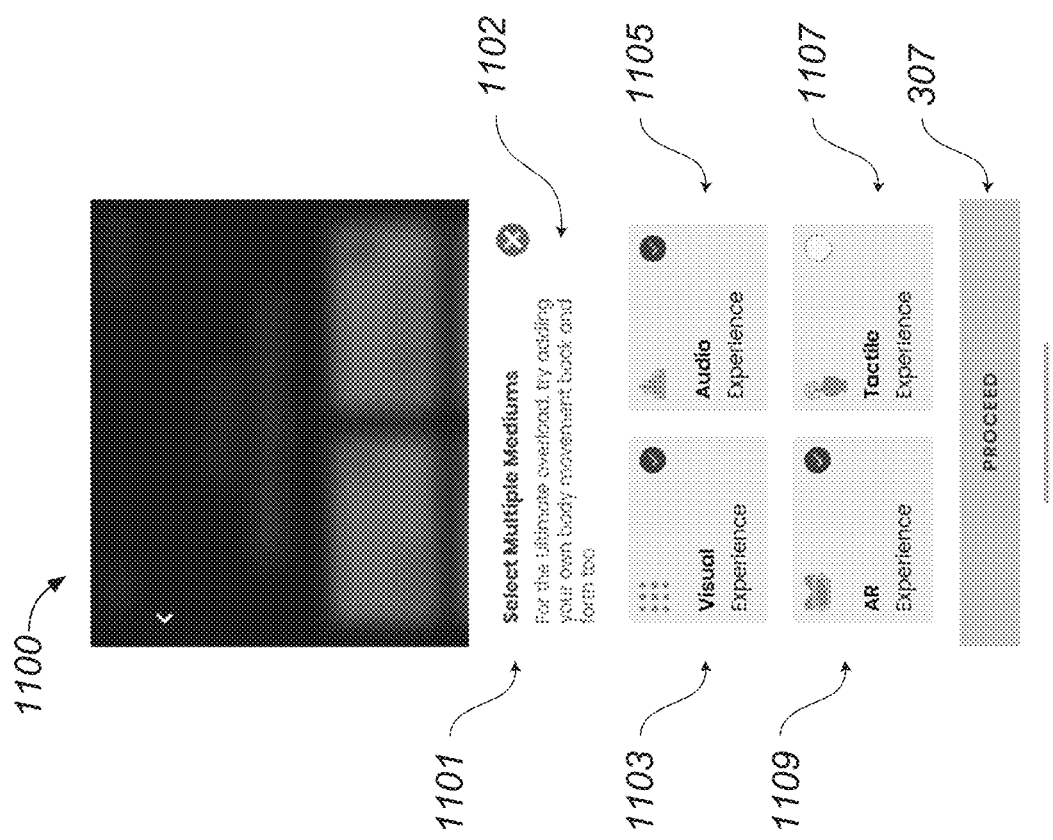

First, screenshot 1100, as shown in FIG. 11A, is provided on the display of touchscreen 131. Screenshot 1100 includes a title 1101, a message 1102 and regions 1103, 1105, 1107, and 1109 for customizing the multi-sensory BLS Session, and a "Proceed" button 307. Title 1101 is the prompt "Select Multiple Mediums", message 1102 is the instruction: "For the Ultimate overload, try adding your own body movement back and forth too." Regions 1103, 1105, 1107, and 1109 include labels text invocative of the type of BLS Session, specifically, region 1103 is labeled "Visual Experience," region 1105 is labeled "Audio Experience," region 1107 is labeled "Tactile Experience," and region 1109 is labeled "AR Experience."

From screenshot 1100, the user must elect two or more of regions 1103, 1105, 1107, and 1109. When a user selects Visual Experience (region 1103), system 100 causes an object to move on a background, similar to what is described above in the section VISUAL BLS SESSION. When a user selects the Audio Experience (region 1105), system 100 provides an audio track that follows the motion of the object, as similar to what is above in the section AV BLS Session. When a user selects the Tactile Experience (region 1107), system 100 requires that the user provide tactile input of the location of the object during a session, as described above in the sections TACTILE BLS SESSION and/or COMPLEX AR BLS SESSION. When a user selects the AR Experience (region 1109), system 100 provides a scene captured by camera 137 to appear as the background on which an object moves, as described above in the section AR BLS SESSION and/or COMPLEX AR BLS SESSION.

After selecting two or more experiences from screenshot 1100, system 100 determines which information must be obtained from the user to configure the configuration, and provides a Multi-Sensory BLS Session configuration screen (not shown) on touchscreen 131 that may include components described above with reference to one or more of screenshots 600, 700, 800, or 900. In certain embodiments, each Multi-Sensory BLS Session configuration screen will include regions 603, 604, 605, 606, and 608 which are used to specify the object type, size, pattern, set duration, and set text message. If the user selection includes an Audio Experience, then the region 702 is used to specify an audio track. If the user selection includes a Tactile Experience, then no additional configurations are required. If the user selection includes a Visual Experience and not an AR Experience, then region 607 is used to specify a background. If the user selects AR Experience, then region includes button 802 to grant access to the camera.

Once the user has configured the session, a screenshot similar to screenshot 1110, as shown in FIG. 11B, is provided on the display of touchscreen 131. Screenshot 1110 is used for the Multi-Sensory BLS Session, and is generally similar to, or combines aspects or components of screenshot 610, 710, 810, and/or 910 to provide the user selected components of the experience.

If the user selects "Tap to Start/Pause" (region 616) during a session, or if the session has reached the end of the set duration, then system 100 determines the next action, as described below with reference to FIGS. 12A-12C, as discussed subsequently.

End of Set Screens

Each session includes one or more repetitions, or sets, as described above in screenshots 610, 710, 810, 910, or 1110. After each set, system 100 provides the display of touchscreen 131 with one or more screens prompting the user for input that is used by system 100 to determine if the set just completed is to be repeated, and/or to evaluate the progress of the user. Examples of screenshots prompting a user for feedback to system 100 after a set is provided in FIGS. 12A, 12B, and 12C.

FIG. 12A is a screenshot 1200 which includes a blurred portion 1201, a prompt 1202, a message 1203, and two response regions 1204 and 1205. Blurred portion 1201 is provided to indicate that the set is over, but may be repeated. Prompt 1202 is "What Comes Up?," and message 1203 is "It may be something you don't think is connected. That's ok. Go back to the picture and hit Repeat. (Repeat until the picture in your mind changes to your liking and you start to believe the positive thoughts about yourself now)." Prompt 1202 and message 1203 instruct the user to recall the picture that they were prompted to think of in screenshot 510 and the positive beliefs refer to those that the user were prompted to consider in screenshot 540.

The user may respond by selecting region 1204, which is labeled: "Repeat," or by selecting region 1205, which is labeled "End Session." If the user selects region 1204, then the set is repeated with the appropriate screenshot 610, 710, 810, 910, or 1110 provided on the display of touchscreen 131. If the user selects region 1205, then the session ends, and system 100 provides a post-session survey, as discussed subsequently.

After every fifth set, the user is provided with some additional screens to evaluate their progress. Thus, after the fifth set, the tenth set, and every additional fifth set, system 100 provides the display of touchscreen 131 with screenshot 1210 as shown in FIG. 12B.

Screenshot 1210 includes blurred portion 1201, a first prompt 301, first prompt response indicia 303, a user adjustable first prompt answer slider 305, a second prompt 1211, second prompt response indicia 1213, a user adjustable second prompt answer slider 1215, and a "Submit" button 1217.

First prompt 301, which is "How much do you believe" "I GOT THIS!" now?," and the indicial and slider are discussed above with reference to FIG. 3B.

Second prompt 1211 is "How much does the picture or issue of "X" bother you now." The text inserted in place of X in prompt 1211 corresponds to the underlined words in the user-selected factor as discussed above with reference to FIG. 3B. Response indicia 1213 ranges from "not at all," with a numerical value of 1, to "worst" with a numerical value of 10, and slider 1215 allows the user to select a response, after which the "Submit" button 1217 is selected.

If the answer selected by slider 1215 has a numerical value greater than 2 then system 100 provides screenshot 1200 on the display of touchscreen 131, as described above regarding FIG. 12A, and the system responds as described above.

If the answer selected by slider 1215 has a numerical value of 2 or less, meaning that the user is showing improvement, then system 100 provides screenshot 1220 on the display of touchscreen 131, as shown in FIG. 12C. Screenshot 1220 includes blurred portion 1201, a prompt 1221, and regions 1223 and 1225 for the user to provide a response to the prompt.

Prompt 1221 is "Do you still believe that your distress level can go down to ZERO?" In response, the user may select either region 1223 ("Yes") or region 1225 ("No"). If the user selects "Yes" (region 1223), then system 100 provides screenshot 1200 on the display of touchscreen 131, and the user may decide to repeat the set or to end the session, as described above. If the user selects "No" (region 1225), then the session ends, and system 100 provides a post-session survey, as discussed subsequently.

Post-Session Survey

After the BLS Session, system 100 further provides the user with an optional post-session survey. Thus, for example and without limitation, system 100 provides the display of touchscreen 131 with sequential prompts to answer, for example and without limitation, four survey questions. The responses to the post-session survey are stored in system 100 as post-session scores. The display of touchscreen 131 for the post-session survey questions may differ from the pre-session survey questions in that a message may emphasize that the question is for a post-session survey. In addition, in some embodiments, the post-session survey questions are presented initially with answers to the same questions from the pre-session survey. The results of the post-session survey, along with the identity of the user, the configuration of the session, and the duration of the session are stored in the memory of system 100.

The first post-session survey question requests that the user report on their level of distress as shown, for example and without limitation, in FIG. 5G as screenshot 570. The first post-session survey question is similar to the sixth pre-session survey question.

The second post-session survey question requires the user to select positive beliefs as shown, for example and without limitation, in FIG. 5E as screenshot 550. The second post-session survey question is similar to the fourth pre-session survey question.

The third post-session survey question requires the user to indicate feelings as shown, for example and without limitation, in FIG. 5F as screenshot 560. The third post-session survey question is similar to the fifth pre-session survey question.

The fourth post-session survey question requires the user to indicate the location of feelings in their body as shown, for example and without limitation, in FIGS. 5H and 5I as screenshots 580 and 590. The fourth post-session survey question is similar to the seventh pre-session survey question.

Post Session Results

FIGS. 13A, 13B, 13C, and 13D are screenshots of touchscreen 131, wherein system 100 presents the user with indicators of progress using the inventive system from the most recent user experience. The information used to generate the screenshots of FIGS. 13A-13D were previously stored in the memory of system 100 from the answers to various pre-session questions and surveys and post-session surveys.

Figures 13A, 13B, 13C:
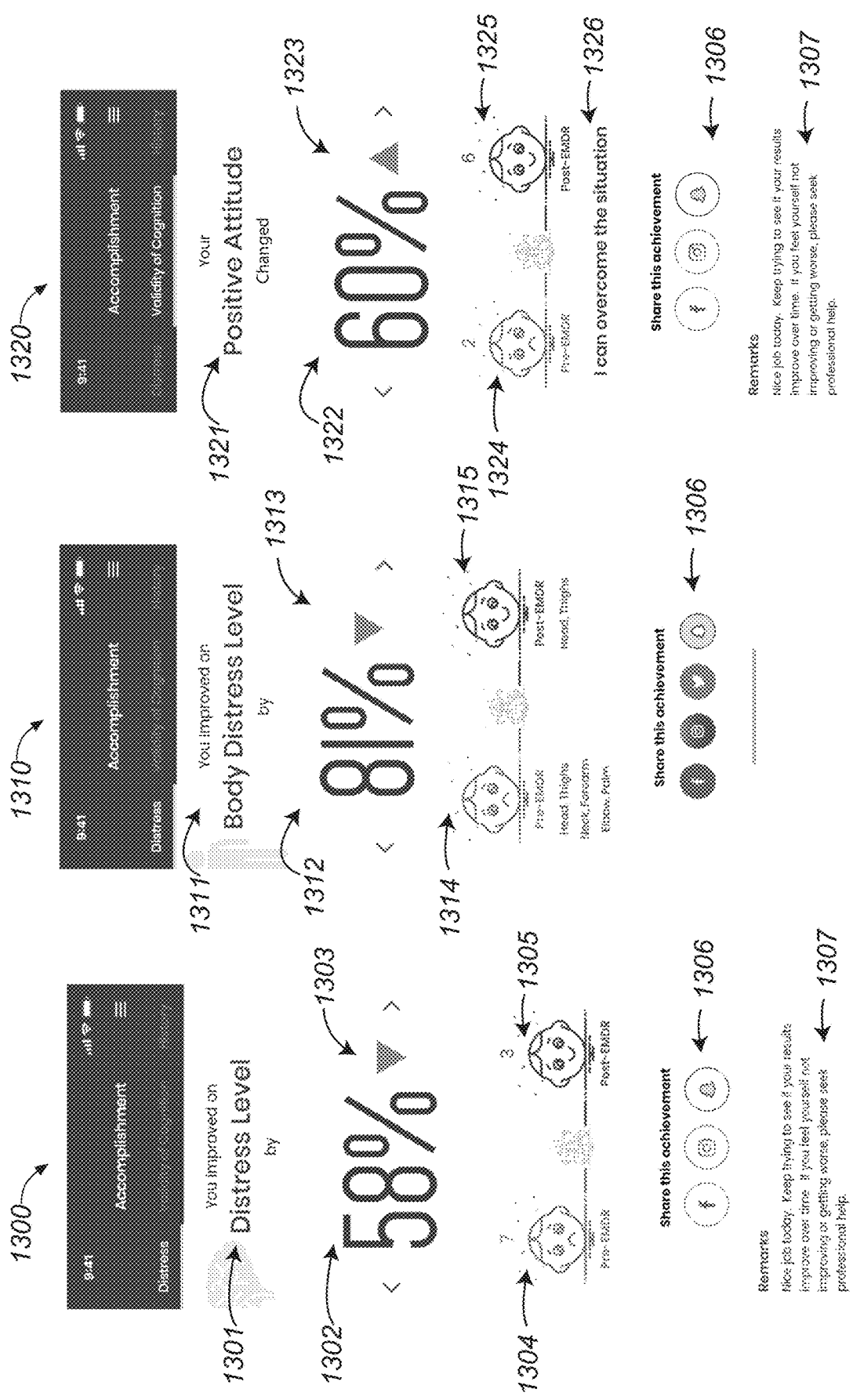

FIG. 13A presents a screenshot 1300 reporting on changes in distress level, and includes a title 1301, a first improvement indicator 1302, a second improvement indicator 1303, a pre-session indicator 1304, a post-session indicator 1305, social media sharing region 1306, and a message 1307.

Title 1301 is "You improved on Distress Level by." First improvement indicator 1301 is the value of the post-session distress score obtained as the answer to the sixth pre-session survey question divided by the value of the pre-session distress score obtained as the answer to the first post-session survey question. Second improvement indicator 1303 is an arrow indicating the direction of the change in distress level, with a downwards facing arrow indicating a decrease from pre-session to post-session. Pre-session indicator 1304 provides the pre-session distress score and a corresponding emoji. Post-session indicator 1305 is the post-session distress score and a corresponding emoji. Social media sharing region 1306 includes icons for popular social media platforms, and system 100 responds to a selection by posting the results of screenshot 1300 on the selected social media platform. Message 1307 includes encouragement and reminds the user to seek professional help, if needed.

FIG. 13B presents a screenshot 1310 reporting on changes in body distress level, and includes a title 1311, a first improvement indicator 1312, a second improvement indicator 1313, a pre-session indicator 1314, a post-session indicator 1315, and social media sharing region 1306 and message 1307.

Title 1311 is "You improved on Body Distress Level by." First improvement indicator 1312 is the percent change in the total number of body parts selected in fourth post-session survey question divided by the total number of body parts selected in the seventh pre-session survey question. Second improvement indicator 1313 is an arrow indicating the direction of the change in body distress level, with a downwards facing arrow indicating a decrease from the pre-session distress score to post-session distress score. Pre-session indicator 1314 provides labels of the selected body parts from the user's answer to the seventh pre-session survey question, and post-session indicator 1315 provides labels of the selected body parts from user's answer to the fourth pre-session survey question.

FIG. 13C presents a screenshot 1320 reporting on changes in the user-selected positive beliefs VOC, and includes a title 1321, one of the user-selected positive beliefs 1326, a first improvement indicator 1322, a second improvement indicator 1323, a pre-session indicator 1324, a post-session indicator 1325, social media sharing region 1306, and a message 1307. In one embodiment, system 100 provides a different screenshot, similar to screenshot 1320, for each of the user-selected positive beliefs, as discussed above.

Title 1321 is "Your Positive Attitude Changed." Positive belief 1326 is one of the positive beliefs that the user selected in response to the third pre-session survey question. First improvement indicator 1322 is, for each user-selected positive belief, the value of the positive belief VOC obtained from the answer to the second post-session survey question divided by the value of the positive belief VOC obtained from the answer to the fourth pre-session survey question. Second improvement indicator 1323 is an arrow indicating the direction of the change in positive belief VOC, with a downwards facing arrow indicating a decrease from the pre-session positive belief VOC to post-session positive belief VOC. Pre-session indicator 1324 provides the pre-session positive belief VOC and a corresponding emoji. Post-session indicator 1325 is the post-session positive belief VOC and a corresponding emoji. Social media sharing region 1306 includes icons for popular social media platforms, and system 100 responds to a selection by posting the results of screenshot 1320 on the selected social media platform. Message 1307 includes encouragement and reminds the user to seek professional help, if needed.

FIG. 13D presents a screenshot 1330 reporting on changes in feelings, and includes a title 1331, a post-session indicator 1333, a pre-session indicator 1335, social media sharing region 1306, and message 1307.

Title 1331 is "Your Feelings." Post-session indicator 1333 lists the feelings provided as answers to the third post-session survey question, and pre-session indicator 1335 lists the feelings provided as answers to the fifth pre-session survey question.

Historical Results

FIGS. 14A, 14B, 14C, and 14D are screenshots of the display of touchscreen 131 presenting the user with historical indicators of progress using the inventive system over some period of time. In the following discussion, current and historic data is retrieved from memory in system 100, and is presented graphically to allow the user to track their progress over time as a function of any of the factors that they have currently or historically selected.

FIG. 14A presents a screenshot 1400 reporting on historical changes in the answer to the first initial question ("How much do you believe I Got This!?), as indicated as message 1403, and includes a time range selector region 1401, a factor selection region 1405, and a graph 1407.

Time range selector region 1401 presents selections for the user to control how much historical information is presented, and may include, for example and without limitation, the last 7, 30, or 180 days, or 1 year or 2 years. When the user selects one of the time ranges, system 100 responds by modifying the x axis of graph 1407.

Factor selection region 1405 presents a drop-down menu of all current and previous selected factors that the user provided in response to the second initial question. System 100 then retrieves all responses to the first initial question for sessions in which the user had selected the factor chosen in region 1405 and for the period of time selected in region 1401, and provides the data in graph 1407.

Graph 1407 thus permits the user to review how much they believe that they can or will improve their relationship to each factor, for any one of the factors that the user currently or previously used system 100 to address.

Figures 14B, 14C, 14D:
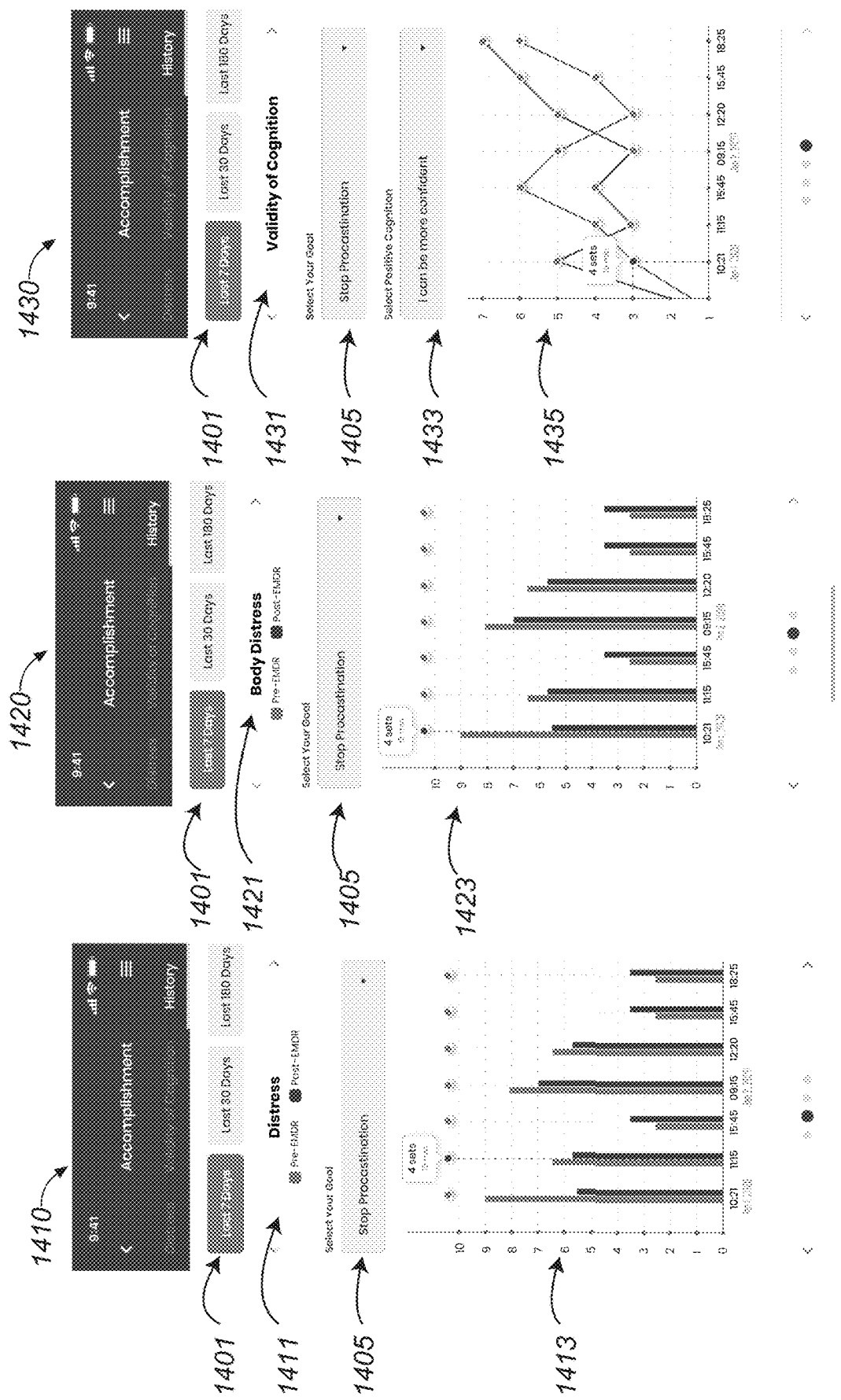

FIG. 14B presents a screenshot 1410 reporting on historical changes in distress level, as indicated as message 1411, and includes time range selector region 1401, factor selection region 1405, and graph 1413.

The user selects a time range using time range selector region 1401, and one of their previously selected factors from factor selection region 1405, as discussed above. System 100 then retrieves all responses to the sixth pre-session survey question and the first post-session survey question, in which the user had selected the factor chosen in region 1405 and for the period of time selected in region 1401, and provides the data in graph 1413.

Graph 1413 thus permits the user to review and compare both the pre-session and post-session distress levels over time as a function of any of their selected factors using system 100.

FIG. 14C presents a screenshot 1420 reporting on historical changes in body distress, as indicated as message 1421, and includes time range selector region 1401, factor selection region 1405, and a graph 1423.

The user selects a time range using time range selector region 1401, and one of their previously selected factors from factor selection region 1405, as discussed above.

System 100 then retrieves all responses to the seventh pre-session survey question and the fourth post-session survey question, in which the user had selected the factor chosen in region 1405 and for the period of time selected in region 1401. Numerical values for body distress are computed by system 100 as discussed above with reference to FIG. 13B, is the percent change in the total number of body parts selected in fourth post-session survey question divided by the total number of body parts selected in the seventh pre-session survey question.

FIG. 13B presents a screenshot 1310 reporting on changes in body distress level, and includes a title 1311, a first improvement indicator 1312, a second improvement indicator 1313, a pre-session indicator 1314, a post-session indicator 1315, and social media sharing region 1306 and message 1307.

Title 1311 is "You improved on Body Distress Level by." First improvement indicator 1312 is the percent change in the total number of body parts selected in fourth post-session survey question divided by the total number of body parts selected in the seventh pre-session survey question. Second improvement indicator 1313 is an arrow indicating the direction of the change in body distress level, with a downwards facing arrow indicating a decrease from the pre-session distress score to post-session distress score. Pre-session indicator 1314 provides labels of the selected body parts from the user's answer to the seventh pre-session survey question, and post-session indicator 1315 provides labels of the selected body parts from user's answer to the fourth pre-session survey question.

Graph 1423 thus permits the user to review and compare the pre-session and post-session body distress over time as a function of any of their selected factors using system 100.

FIG. 14D presents a screenshot 1430 reporting on historical changes in positive belief VOC, as indicated as message 1431, and includes time range selector region 1401, factor selection region 1405, a positive belief selector 1433, and a graph 1435.

The user selects a time range using time range selector region 1401, and one of their previously selected factors from factor selection region 1405, as discussed above. The user further selects a positive belief from selector 1433, which includes answers to all of the third pre-session survey questions that the user has answered.

System 100 then retrieves all responses to the fourth pre-session survey question and the second post-session survey question in which the user had selected the factor chosen in region 1405 and positive belief from selector 1433, and for the period of time selected in region 1401, and provides the data in graph 1435.

Graph 1435 thus permits the user to review and compare changes in pre-session and post-session positive belief VOC for a given factor over time as a function of any of their selected factors using system 100.

Thus, as will be appreciated by those skilled in the art, embodiments of the present invention may be embodied as a method, an apparatus such as a special purpose apparatus, an apparatus such as a data processing system, or a carrier medium, e.g., a computer program product. The carrier medium carries one or more computer readable code segments for controlling a processing system to implement a method. Accordingly, aspects of the present invention may take the form of a method, an entirely hardware embodiment, an entirely software embodiment or an embodiment combining software and hardware aspects. Furthermore, the present invention may take the form of carrier medium (e.g., a computer program product on a computer-readable storage medium) carrying computer-readable program code segments embodied in the medium. Any suitable computer readable medium may be used including a magnetic storage device such as a diskette or a hard disk, or an optical storage device such as a CD-ROM.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

Similarly, it should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Thus, while there has been described what is believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used, and the functionality described may be performed on one or more networked devices. Steps may be added or deleted to methods and functions provided by the apparatus described are within the scope of the present invention.

I claim:

1. A method of using an electronic device having a display screen, an input device, and a camera for a bilateral stimulation (BLS) session for a user, said method comprising:

providing the display screen with a prompt to the user to select one or more stimuli for the BLS session, where the user addresses a mental-health factor during the BLS session, where the factor is a problem or a goal, where the BLS session includes a first visual stimuli on the display screen including a virtual object that moves in a BLS inducing pattern on the display screen, where the object is related to the factor, a second visual stimuli, including a background for the object on the display screen, where the background is a real-time display of the scene obtained from the camera, and a tactile stimuli input to the input device, where the tactile input requires that the user periodically identify a location of the object on a scene on the display screen to continue the BLS session, providing the BLS session on the electronic device including the selected stimuli, where the pattern is determined from two or more sequential locations in the scene, where the two or more sequential locations of the object in the scene alternate repeatedly between a left side or a right side of scene relative to the display screen, and where a BLS session includes, for each location of the two or more sequential locations in the scene:

determining the location of the object in the scene;

determining an active area of the display screen, where the active area is the only portion of the display screen in which the image of the object is displayed;

determining a current position on the display screen of the location in the scene;

displaying an image of the object on the display screen based on the current position on the display screen being within the active area of the display screen; and waiting until the user identifies the image on the display screen using the input device.

2. The method of claim 1, where the prompt further includes the prompt for the selection of an audio stimuli, where the method further comprises providing a user-selected audio to a left audio channel and to a right audio channel, and where, for the audio stimuli, the audio output of the left audio channel and of right audio channel track a right/left motion of the object in the pattern.

3. The method of claim 2, where the method further includes accepting the user-selected audio from the electronic device or from the Internet.

4. The method of claim 1, where the prompt further includes the prompt for the selection of the third visual stimuli and where the text message of the third visual stimuli is a user-supplied text message.

5. The method of claim 4, where the text message of the third visual stimuli is a user-selected message.

* * * * *